(12) United States Patent
Finkelstein et al.

(10) Patent No.: US 8,012,499 B2
(45) Date of Patent: Sep. 6, 2011

(54) ANTHRANILAMIDES FOR CONTROLLING INVERTEBRATE PESTS

(75) Inventors: Bruce Lawrence Finkelstein, Newark, DE (US); Stephen Frederick McCann, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 706 days.

(21) Appl. No.: 11/989,348

(22) PCT Filed: Aug. 22, 2006

(86) PCT No.: PCT/US2006/032726
§ 371 (c)(1),
(2), (4) Date: Jan. 23, 2008

(87) PCT Pub. No.: WO2007/024833
PCT Pub. Date: Mar. 1, 2007

(65) Prior Publication Data
US 2009/0269300 A1 Oct. 29, 2009

Related U.S. Application Data

(60) Provisional application No. 60/711,030, filed on Aug. 24, 2005.

(51) Int. Cl.
*A01N 25/00* (2006.01)
*A01N 43/40* (2006.01)
*A01N 43/64* (2006.01)
*A01N 43/56* (2006.01)
*A01N 43/36* (2006.01)
*A61K 31/435* (2006.01)
*A61K 31/44* (2006.01)
*A61K 31/41* (2006.01)
*A61K 31/415* (2006.01)
*A61K 31/40* (2006.01)

(52) U.S. Cl. ........ 424/405; 514/277; 514/339; 514/341; 514/359; 514/403; 514/406; 514/408

(58) Field of Classification Search .................. None
See application file for complete search history.

(56) References Cited

U.S. PATENT DOCUMENTS

| | | | |
|---|---|---|---|
| 6,747,047 B2 | 6/2004 | Lahm et al. |
| 6,965,032 B2 | 11/2005 | Freudenberger |
| 6,995,178 B2 | 2/2006 | Lahm et al. |
| 7,038,057 B2 | 5/2006 | Annis et al. |
| 7,087,598 B2 | 8/2006 | Clark |
| 7,148,217 B2 | 12/2006 | Selby |
| 7,157,475 B2 | 1/2007 | Clark |
| 7,179,824 B2 | 2/2007 | Zimmerman |
| 7,199,138 B2 | 4/2007 | Finkelstein et al. |
| 7,211,270 B2 | 5/2007 | Lahm et al |
| 7,227,025 B2 | 6/2007 | Freudenberger |
| 7,232,836 B2 | 6/2007 | Lahm et al. |
| 7,241,767 B2 | 7/2007 | Clark et al. |
| 7,247,647 B2 | 7/2007 | Hughes et al. |
| 7,276,601 B2 | 10/2007 | Taylor |
| 7,288,554 B2 | 10/2007 | Finkelstein et al. |
| 7,335,780 B2 | 2/2008 | Annis |
| 7,338,978 B2 | 3/2008 | Lahm et al. |
| 7,339,057 B2 | 3/2008 | Taylor |
| 7,375,232 B2 | 5/2008 | Clark et al. |
| 2004/0102324 A1 | 5/2004 | Annis et al. |
| 2004/0110777 A1 | 6/2004 | Annis et al. |
| 2004/0209923 A1 | 10/2004 | Berger et al. |
| 2004/0235959 A1 | 11/2004 | Lahm et al. |
| 2005/0075372 A1 | 4/2005 | Lahm et al. |
| 2005/0147633 A1 | 7/2005 | Stevenson |
| 2006/0014808 A1 | 1/2006 | Hughes et al. |
| 2006/0167060 A1 | 7/2006 | Lahm et al. |
| 2006/0205748 A1 | 9/2006 | Annis et al. |
| 2007/0021468 A1 | 1/2007 | Annis |
| 2007/0161797 A1 | 7/2007 | Shapiro |
| 2007/0184018 A1 | 8/2007 | Lahm et al. |
| 2007/0299265 A1 | 12/2007 | Shapiro et al. |
| 2008/0027046 A1 | 1/2008 | Annan et al. |
| 2008/0108821 A1 | 5/2008 | Taylor |
| 2008/0177078 A1 | 7/2008 | Fagan |

FOREIGN PATENT DOCUMENTS

| | | |
|---|---|---|
| EP | 0991625 B1 | 6/2005 |
| WO | WO98/28269 | 7/1998 |
| WO | WO98/57937 | 12/1998 |
| WO | WO03/015519 A1 | 2/2003 |
| WO | WO03/016300 A1 | 2/2003 |
| WO | WO03/106427 A2 | 12/2003 |
| WO | WO2006/023783 | 3/2006 |
| WO | WO2006/055922 | 5/2006 |
| WO | WO2006/068669 | 6/2006 |

OTHER PUBLICATIONS

Heller, Gustav, "New Isomerisms in the Isatin Series, V", Berichte Der Deutschen Chemischem Gesellschaft [Abteilung] B: Abhandlungen, 55B, 2681-97 (1922) & Chemical Abstracts Service, Columbus, OH, database accession No. 1923:5524.

*Primary Examiner* — Ernst Arnold
(74) *Attorney, Agent, or Firm* — Reed A. Coats

(57) ABSTRACT

Disclosed are compounds of Formula (1), including all geometric and stereoisomers, N-oxides, and salts thereof, wherein $R^3$ is —C(=B)C(=O)L or —C($R^{11}R^{12}$)C(=O)L; $R^4$ is, inter alia, H, $C_1$-$C_4$ alkyl or $C_2$-$C_6$ alkoxycarbonyl; or $R^3$ and $R^4$ are taken together as —C(=O)C(=O)—, —C(=$NR^{13}$)C(=O)— or —C($R^{11}R^{12}$)C(=O)—. B is O, $NR^{13}$, $NOR^{13}$ Or $NNR^{14}R^{15}$; L is OH or $NR^{14}R^{15}$; and X, $R^1$, $R^2$, $R^{11}$, $R^{12}$, $R^{13}$, $R^{14}$, $R^{15}$ and J are as defined in the disclosure. Also disclosed are compositions containing the compounds of Formula (1) and methods for controlling an invertebrate pest comprising contacting the invertebrate pest or its environment with a biologically effective amount of a compound or a composition of the invention.

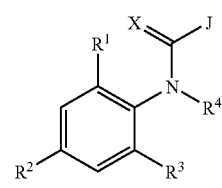

(1)

20 Claims, No Drawings

ANTHRANILAMIDES FOR CONTROLLING INVERTEBRATE PESTS

FIELD OF THE INVENTION

This invention relates to certain anthranilamides, their N-oxides, salts and compositions suitable for agronomic and nonagronomic uses, and methods of their use for controlling invertebrate pests such as arthropods in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public and animal health is also important. Many products are commercially available for these purposes, but the need continues for new compounds which are more effective, less costly, less toxic, environmentally safer or have different modes of action.

WO 03/015519 discloses N-acyl anthranilic acid derivatives of Formula i as anthropodicides wherein, inter alia, $R^1$ is $CH_3$, F, Cl or Br; $R^2$ is F, Cl, Br, I or $CF_3$; $R^3$ is $CF_3$, Cl, Br or $OCH_2CF_3$; $R^{4a}$ is $C_1$-$C_4$ alkyl; $R^{4b}$ is H or $CH_3$; and $R^5$ is Cl or Br.

SUMMARY OF THE INVENTION

This invention is directed to compounds of Formula 1 including all geometric isomers and stereoisomers, N-oxides, and salts thereof, agricultural and nonagricultural compositions containing them and their use for controlling invertebrate pests:

wherein:
X is O or S;
J is a phenyl optionally substituted with one to four substituents independently selected from $R^5$; or
J is a heterocyclic ring selected from the group consisting of $R^1$ is $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, —CN, —CHO, —$NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_2$-$C_4$ alkylcarbonyl, $C_2$-$C_4$ alkoxycarbonyl, $C_2$-$C_4$ alkylaminocarbonyl, $C_3$-$C_5$ dialkylaminocarbonyl, $C_1$-$C_4$ alkylamino or $C_2$-$C_6$ dialkylamino;
$R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ haloalkyl, halogen, —CN, —CHO, —NO$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_2$-$C_4$ alkylcarbonyl, $C_2$-$C_4$ alkoxycarbonyl, $C_2$-$C_4$ alkylaminocarbonyl, $C_3$-$C_5$ dialkylaminocarbonyl, $C_1$-$C_4$ alkylamino or $C_2$-$C_6$ dialkylamino;

$R^3$ is —C(=B)C(=O)L or —C($R^{11}R^{12}$)C(=O)L;

$R^4$ is H; or $C_1$-$C_6$ alkyl, $C_2$-$C_6$ alkenyl, $C_2$-$C_6$ alkynyl or $C_3$-$C_6$ cycloalkyl, each optionally substituted with one or more substituents selected from the group consisting of halogen, —CN, —NO$_2$, hydroxy, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^4$ is $C_2$-$C_6$ alkylcarbonyl, $C_2$-$C_6$ alkoxycarbonyl, $C_2$-$C_6$ alkylaminocarbonyl or $C_3$-$C_8$ dialkylaminocarbonyl; or $R^3$ and $R^4$ are taken together as —C(=B)C(=O)— or —C($R^{11}R^{12}$)C(=O)—, wherein the left-hand of these moieties is bonded as $R^3$ and the right-hand as $R^4$;

each $R^5$ is independently $C_1$-$C_6$ alkyl, $C_3$-$C_6$ cycloalkyl, $C_1$-$C_6$ haloalkyl, halogen, —CN, $C_1$-$C_4$ alkoxy, $C_1$-$C_4$ alkylthio, $C_1$-$C_4$ haloalkoxy, $C_1$-$C_4$ haloalkylthio, $C_1$-$C_4$ haloalkylsulfinyl or $C_1$-$C_4$ haloalkylsulfonyl; or phenyl or pyridyl, each optionally substituted with one to three $R^9$;

$R^6$ is H, $C_1$-$C_6$ alkyl, $C_3$-$C_6$ cycloalkyl, $C_1$-$C_6$ haloalkyl, halogen, —CN, $C_1$-$C_4$ alkoxy, $C_2$-$C_4$ alkoxycarbonyl, $C_1$-$C_4$ alkylthio, $C_1$-$C_4$ haloalkoxy, $C_1$-$C_4$ haloalkylthio, $C_1$-$C_4$ haloalkylsulfinyl or $C_1$-$C_4$ haloalkylsulfonyl;

$R^7$ is $C_1$-$C_6$ alkyl optionally substituted with one or more substituents selected from the group consisting of halogen, —CN, —NO$_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^7$ is phenyl or pyridyl, each optionally substituted with one to three substituents selected from $R^9$;

$R^8$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl;

each $R^9$ is independently $C_1$-$C_6$ alkyl, $C_3$-$C_6$ cycloalkyl, $C_1$-$C_6$ haloalkyl, halogen, —CN, $C_1$-$C_4$ alkoxy, $C_1$-$C_4$ alkylthio, $C_1$-$C_4$ haloalkoxy, $C_1$-$C_4$ haloalkylthio, $C_1$-$C_4$ haloalkylsulfinyl or $C_1$-$C_4$ haloalkylsulfonyl;

$R^{11}$ and $R^{12}$ are independently H; halogen; —CN; O$R^{13}$; or $C_1$-$C_6$ alkyl, $C_2$-$C_6$ alkenyl, $C_2$-$C_6$ alkynyl or $C_3$-$C_6$ cycloalkyl, each optionally substituted with one or more halogen;

B is O, N$R^{13}$, NO$R^{13}$ or NN$R^{14}R^{15}$;

L is OH or N$R^{14}R^{15}$;

$R^{13}$ is H; or $C_1$-$C_6$ alkyl, $C_2$-$C_6$ alkenyl, $C_2$-$C_6$ alkynyl or $C_3$-$C_6$ cycloalkyl, each optionally substituted with one or more halogen;

$R^{14}$ and $R^{15}$ are independently H; G; or $C_1$-$C_6$ alkyl, $C_2$-$C_6$ alkenyl or $C_2$-$C_6$ alkynyl, each optionally substituted with one or more substituents selected from the group consisting of G, halogen, —CN, —NO$_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_4$ alkylcarbonyl, $C_2$-$C_4$ alkoxycarbonyl, $C_1$-$C_4$ alkylamino, $C_2$-$C_8$ dialkylamino and $C_3$-$C_6$ cycloalkylamino; or $R^{14}$ and $R^{15}$ are taken together with the nitrogen to which they are attached to form a ring containing 2 to 6 atoms of carbon and optionally one additional atom of nitrogen, sulfur or oxygen, said ring optionally substituted with 1 to 4 substituents selected from the group consisting of $C_1$-$C_2$ alkyl, halogen, —CN, —NO$_2$ and $C_1$-$C_2$ alkoxy; and each G is independently a 3- to 6-membered nonaromatic carbocyclic or heterocyclic ring, optionally including one or two ring members selected from the group consisting of C(=O), S(O) or S(O)$_2$ and optionally substituted with 1 to 4 substituents selected from the group consisting of $C_1$-$C_2$ alkyl, halogen, —CN, —NO$_2$ and $C_1$-$C_2$ alkoxy.

This invention also provides a composition comprising a compound of Formula 1 and at least one additional component selected from the group consisting of a surfactant, a solid diluent and a liquid diluent. In one embodiment, this invention also provides a composition for controlling an invertebrate pest comprising a biologically effective amount of a compound of Formula 1 and at least one additional component selected from the group consisting of a surfactant, a solid diluent and a liquid diluent, said composition optionally further comprising a biologically effective amount of at least one additional biologically active compound or agent.

This invention further provides a spray composition for controlling an invertebrate pest comprising a biologically effective amount of a compound of Formula 1 or the composition described in the embodiment above and a propellant. This invention also provides a bait composition for controlling an invertebrate pest comprising a biologically effective amount of a compound of Formula 1 or the composition described in the embodiment above, one or more food materials, optionally an attractant, and optionally a humectant.

This invention further provides a trap device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

This invention also provides a method for controlling an invertebrate pest comprising contacting the invertebrate pest or its environment with a biologically effective amount of a compound of Formula 1 (e.g., as a composition described herein). This invention also relates to such method wherein the invertebrate pest or its environment is contacted with a composition comprising a biologically effective amount of a compound of Formula 1 and at least one additional component selected from the group consisting of a surfactant, a solid diluent and a liquid diluent, said composition optionally further comprising a biologically effective amount of at least one additional biologically active compound or agent.

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular. For example, a composition of the present invention comprises a biologically effective amount of "a" compound of Formula 1 which should be read that the composition includes one or at least one compound of Formula 1.

In the above recitations, the term "alkyl", used either alone or in compound words such as "alkylthio" or "haloalkyl" includes straight-chain or branched alkyl, such as, methyl, ethyl, ii-propyl, i-propyl, or the different butyl, pentyl or hexyl isomers. The term "1-2 alkyl" indicates that one or two of the available positions for that substituent may be alkyl which are independently selected. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Cycloalkyl" includes, for example, cyclopropyl, cyclobutyl, cyclopentyl, and cyclohexyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio and butylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl isomers. "Alkylamino", "dialkylamino", "cycloalkylamino", and the like, are defined analogously to the above examples.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said allyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$. "Alkylcarbonyl" denotes a straight-chain or branched alkyl moieties bonded to a $C(=O)$ moiety. Examples of "alkylcarbonyl" include $CH_3C(=O)-$, $CH_3CH_2CH_2C(=O)-$ and $(CH_3)_2CHC(=O)-$. Examples of "alkoxycarbonyl" include $CH_3C(=O)-$, $CH_3CH_2C(=O)-$, $CH_3CH_2CH_2OC(=O)-$, $(CH_3)_2CHOC(=O)-$ and the different butoxy- or pentoxy-carbonyl isomers. Examples of "alkylaminocarbonyl" include $CH_3NHC(=O)-$, $CH_3CH_2NHC(=O)-$, $CH_3CH_2CH_2NHC(=O)-$, $(CH_3)_2CHNHC(=O)-$ and the different butylamino- or pentylaminocarbonyl isomers. Examples of "dialkylaminocarbonyl" include $(CH_3)_2NC(=O)-$, $(CH_3CH_2)_2NC(=O)-$, $CH_3CH_2(CH_3)NC(=O)-$, $(CH_3)_2CHN(CH_3)C(=O)-$ and $CH_3CH_2CH_2(CH_3)NC(=O)-$.

The total number of carbon atoms in a substituent group is indicated by the "$C_i$-$C_j$" prefix where i and j are numbers from 1 to 8. For example, $C_1$-$C_4$ alkylsulfonyl designates methylsulfonyl through butylsulfonyl.

The term "nonaromatic carbocyclic ring" denotes fully saturated carbocyclic rings as well as partially or fully unsaturated carbocyclic rings where the Hückel rule is not satisfied. The term "nonaromatic heterocyclic ring" denotes fully saturated heterocyclic rings as well as partially or fully unsaturated heterocyclic rings where the Hückel rule is not satisfied. The heterocyclic ring systems can be attached through any available carbon or nitrogen by replacement of a hydrogen on said carbon or nitrogen. The term "optionally substituted" in connection with aromatic ring groups refers to groups that are unsubstituted or have at least one non-hydrogen substituent. Commonly, the number of optional substituents (when present) ranges from one to four.

In the above recitations, when a compound of Formula 1 is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R^5)_{1-4}$, then the number of substituents may be selected from the integers between 1 and 4 inclusive. When a group contains a substituent which can be hydrogen, for example $R^2$ or $R^6$, then, when this substituent is taken as hydrogen, it is recognized that this is equivalent to said group being unsubstituted.

One skilled in the art recognizes that "pyridinyl" and "pyridyl" are equivalent alternative names for an organic radical formed by removing a hydrogen atom from a pyridine ring to form an attachment point; accordingly "pyridinyl" and "pyridyl" are used herein as synonyms.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers, or as an optically active form.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature; see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid. Accordingly, the present invention comprises compounds selected from Formula 1, N-oxides and agriculturally suitable salts thereof.

As noted above, G is a 3- to 6-membered nonaromatic carbocyclic or heterocyclic ring, optionally including one or two ring members selected from the group consisting of C(=O), S(O) or S(O)$_2$ and optionally substituted with 1 to 4 substituents selected from the group consisting of C$_1$-C$_2$ alkyl, halogen, —CN, —NO$_2$ and C$_1$-C$_2$ alkoxy. Examples of 3- to 6-membered nonaromatic carbocyclic or heterocyclic rings include those illustrated as G-1 through G-45 in Exhibit 1. Note that the attachment point on these G groups is illustrated as floating; the G group can be attached to the remainder of Formula 1 through any available carbon or nitrogen of the G group by replacement of a hydrogen atom. The optional substituents can be attached to any carbon or nitrogen by replacement of a hydrogen atom (said substituents are not illustrated in Exhibit 1 since they are optional substituents). Note that when G comprises a ring selected from G-24 through G-31, G-34 and G-35, Q$^2$ may be selected from O, S, NH or substituted N.

Exhibit 1

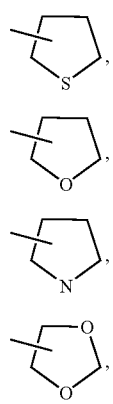

G-1, G-2, G-3, G-4

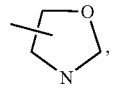 G-5,

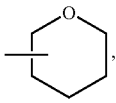 G-6,

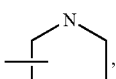 G-7,

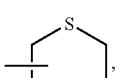 G-8,

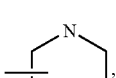 G-9,

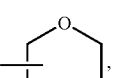 G-10,

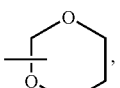 G-11,

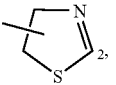 G-12,

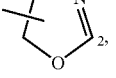 G-13,

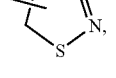 G-14,

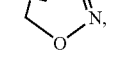 G-15,

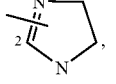 G-16,

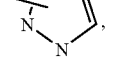 G-17,

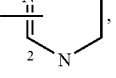 G-18,

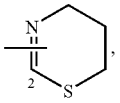 G-19,

-continued

G-20 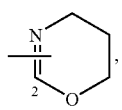

G-21 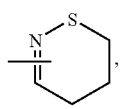

G-22 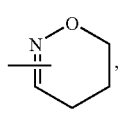

G-23 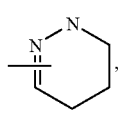

G-24 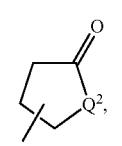

G-25 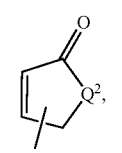

G-26 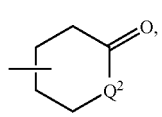

G-27 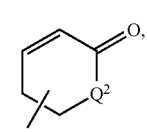

G-28 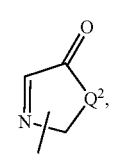

G-29 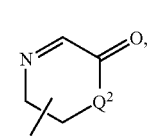

G-30 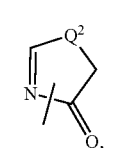

G-31 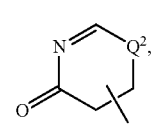

-continued

G-32 

G-33 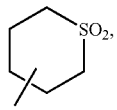

G-34 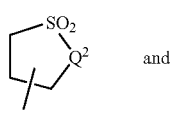 and

G-35 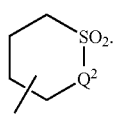

G-36 

G-37

G-38 

G-39

G-40

G-41 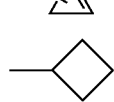

G-42

G-43 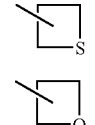

G-44

G-45 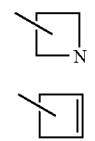

Embodiments of the present invention include:

Embodiment 1A. A compound of Formula 1 wherein $R^1$ is $C_1$-$C_4$ alkyl, $C_1$-$C_4$ haloalkyl, halogen, —CN, $C_1$-$C_4$ alkoxy or $C_1$-$C_4$ haloalkoxy.

Embodiment 1B. A compound of Embodiment 1A wherein $R^1$ is $CH_3$, $CF_3$, $OCF_3$, $OCHF_2$, —CN or halogen.

Embodiment 1C. A compound of Embodiment 1B wherein $R^1$ is $CH_3$, F, Cl, Br or I.

Embodiment 1D. A compound of Embodiment 1C wherein $R^1$ is $CH_3$, Cl, Br or I.

Embodiment 1E. A compound of Embodiment 1D wherein $R^1$ is $CH_3$ or Cl.

Embodiment 2A. A compound of Formula 1 wherein $R^2$ is H, $C_1$-$C_4$ alkyl, $C_1$-$C_4$ haloalkyl, halogen, —CN, —CHO, —$NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl.

Embodiment 2B. A compound of Embodiment 2A wherein $R^2$ is H, $CH_3$, $CF_3$, $OCF_3$, $OCHF_2$, $S(O)_p CF_3$, $S(O)_p CHF_2$, —CN or halogen; and p is 0, 1 or 2.

Embodiment 2C. A compound of Embodiment 2B wherein $R^2$ is H, $CH_3$, $CF_3$, —CN, F, Cl, Br or I.

Embodiment 2D. A compound of Embodiment 2C wherein $R^2$ is $CH_3$, —CN, F, Cl, Br or I.

Embodiment 2E. A compound of Embodiment 2D wherein $R^2$ is Cl, Br or —CN.

Embodiment 2F. A compound of Embodiment 2E wherein $R^2$ is Cl or Br.

Embodiment 2G. A compound of Embodiment 2E wherein $R^2$ is —CN.

Embodiment 3A. A compound of Formula 1 wherein $R^3$ is —C(=O)C(=O)OH, —C(=NR$^{13}$)C(=O)OH or —C(R$^{11}$R$^{12}$)C(=O)OH.

Embodiment 3B. A compound of Embodiment 3A wherein $R^3$ is —C(=O)C(=O)OH.

Embodiment 3C. A compound of Formula 1 wherein $R^3$ is —C(=O)C(=O)NR$^{14}$R$^{15}$, —C(=NR$^{13}$)C(=O)NR$^{14}$R$^{15}$ or —C(R$^{11}$R$^{12}$)C(=O)NR$^{14}$R$^{15}$.

Embodiment 3D. A compound of Embodiment 3C wherein $R^3$ is —C(=O)C(=O)NR$^{14}$R$^{15}$.

Embodiment 3E. A compound of Formula 1 wherein $R^3$ is —C(=O)C(=O)OH, —C(R$^{11}$R$^{12}$)C(=O)OH, —C(=O)C(=O)NR$^{14}$R$^{15}$ or —C(R$^{11}$R$^{12}$)C(=O)NR$^{14}$R$^{15}$.

Embodiment 4A. A compound of Formula 1 wherein $R^4$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl.

Embodiment 4B. A compound of Embodiment 4A wherein $R^4$ is H.

Embodiment 5A. A compound of Formula 1 wherein $R^3$ and $R^4$ are taken together as —C(=O)C(=O)—, —C(=NR$^{13}$)C(=O)— or —C(R$^{11}$R$^{12}$)C(=O)—.

Embodiment 5B. A compound of Embodiment 5A wherein $R^3$ and $R^4$ are taken together as —C(=O)C(=O)—.

Embodiment 6A. A compound of Formula 1 wherein each $R^5$ is independently $C_1$-$C_4$ alkyl, $C_1$-$C_4$ haloalkyl, halogen, —CN, $C_1$-$C_4$ alkoxy or $C_1$-$C_4$ haloalkoxy.

Embodiment 6B. A compound of Embodiment 6A wherein each $R^5$ is independently $CH_3$, $CF_3$, halogen, —CN, $OCH_3$, $OCF_3$ or $OCHF_2$.

Embodiment 6C. A compound of Embodiment 6B wherein each $R^5$ is independently $CF_3$, F, Cl, Br, —CN, $OCF_3$ or $OCHF_2$.

Embodiment 6D. A compound of Embodiment 6C wherein each $R^5$ is independently $CF_3$, $OCF_3$ or $OCHF_2$.

Embodiment 7A. A compound of Formula 1 wherein each $R^6$ is independently $C_1$-$C_4$ haloalkyl, halogen, —CN or $C_1$-$C_4$ haloalkoxy.

Embodiment 7B. A compound of Embodiment 7A wherein each $R^6$ is independently halogen, $C_1$-$C_2$ fluoroalkoxy or $C_1$-$C_2$ fluoroalkyl.

Embodiment 7C. A compound of Embodiment 7B wherein each $R^6$ is independently halogen, $OCH_2CF_3$, $OCHF_2$ or $CF_3$.

Embodiment 7D. A compound of Embodiment 7C wherein each $R^6$ is independently Cl, Br, $OCH_2CF_3$ or $CF_3$.

Embodiment 8A. A compound of Formula 1 wherein $R^7$ is a phenyl ring optionally substituted with one to three substituents independently selected from $R^9$.

Embodiment 8B. A compound of Embodiment 8A wherein each $R^9$ is independently $C_1$-$C_4$ alkyl, $C_1$-$C_4$ haloalkyl, halogen or —CN.

Embodiment 8C. A compound of Embodiment 8B wherein each $R^9$ is independently $CH_3$, $CF_3$, —CN or halogen.

Embodiment 9A. A compound of Formula 1 wherein $R^7$ is

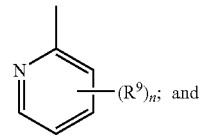

n is 0, 1, 2 or 3.

Embodiment 9B. A compound of Embodiment 9A wherein each $R^9$ is independently $C_1$-$C_4$ alkyl, $C_1$-$C_4$ haloalkyl, halogen or —CN; and n is 0, 1 or 2.

Embodiment 9C. A compound of Embodiment 9B wherein each $R^9$ is independently $CH_3$, $CF_3$, —CN or halogen.

Embodiment 10A. A compound of Formula 1 wherein each $R^8$ is $C_1$-$C_4$ alkyl or $C_1$-$C_4$ haloalkyl.

Embodiment 10B. A compound of Embodiment 10A wherein $R^8$ is $C_1$-$C_4$ haloalkyl.

Embodiment 10C. A compound of Embodiment 10B wherein $R^8$ is $C_1$-$C_2$ fluoroalkyl.

Embodiment 10D. A compound of Embodiment 10C wherein $R^8$ is $CH_2CF_3$ or $CHF_2$.

Embodiment 11A. A compound of Formula 1 wherein $R^{11}$ and $R^{12}$ are independently H or $C_1$-$C_4$ alkyl.

Embodiment 11B. A compound of Embodiment 11A wherein $R^{11}$ and $R^{12}$ are independently H or $CH_3$.

Embodiment 12A. A compound of Formula 1 wherein $R^{13}$ is H or $C_1$-$C_4$ alkyl.

Embodiment 12B. A compound of Embodiment 12A wherein $R^{13}$ is H or $CH_3$.

Embodiment 13A. A compound of Formula 1 wherein $R^{14}$ and $R^{15}$ are independently H; or $C_1$-$C_6$ alkyl, $C_2$-$C_6$ alkenyl, $C_2$-$C_6$ alkynyl or $C_3$-$C_6$ cycloalkyl, each optionally substituted with one or more halogen or —CN.

Embodiment 13B. A compound of Embodiment 13A wherein $R^{14}$ and $R^{15}$ are independently H, $C_1$-$C_4$ alkyl, $C_2$-$C_4$ alkenyl, $C_2$-$C_4$ alkynyl or $C_3$-$C_6$ cycloalkyl.

Embodiment 14A. A compound of Formula 1 wherein J is a heterocyclic ring selected from the group consisting of J-1, J-2 and J-3.

Embodiment 14B. A compound of Formula 1 wherein J is J-1 or J-2.

Embodiment 14C. A compound of Formula 1 wherein J is J-1 or J-3.

Embodiment 14D. A compound of Formula 1 wherein J is J-2 or J-3.

Embodiment 14E. A compound of Formula 1 wherein J is J-1.

Embodiment 14F. A compound of Formula 1 wherein J is J-2.

Embodiment 14G. A compound of Formula 1 wherein J is J-3.

Embodiment 14H. A compound of Formula 1 wherein J is J-4.

Embodiment 14I. A compound of Formula 1 wherein J is J-5.

Embodiment 14J. A compound of Formula 1 wherein J is J-6.

Embodiment 14K. A compound of Formula 1 wherein J is J-7.

Embodiment 14L. A compound of Formula 1 wherein J is J-8.

Combinations of Embodiments 1A-14L are illustrated by:

Embodiment A. A compound of Formula 1 wherein
$R^1$ is $C_1$-$C_4$ alkyl, $C_1$-$C_4$ haloalkyl, halogen, —CN, $C_1$-$C_4$ alkoxy or $C_1$-$C_4$ haloalkoxy;
$R^2$ is H, $C_1$-$C_4$ alkyl, $C_1$-$C_4$ haloalkyl, halogen, —CN, —CHO, —NO$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl;
$R^3$ is —C(=O)C(=O)OH, —C($R^{11}R^{12}$)C(=O)OH, —C(=O)C(=O)N$R^{14}R^{15}$ or —C($R^{11}R^{12}$)C(=O)N$R^{14}R^{15}$; and
$R^4$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl; or
$R^3$ and $R^4$ are taken together as —C(=O)C(=O)—, —C(=N$R^{13}$)C(=O)— or —C($R^{11}R^{12}$)C(=O)—.

Embodiment B. A compound of Embodiment A wherein
$R^1$ is $CH_3$, $CF_3$, $OCF_3$, $OCHF_2$, —CN or halogen;
$R^2$ is H, $CH_3$, $CF_3$, $OCF_3$, $OCHF_2$, $S(O)_pCF_3$, $S(O)_pCHF_2$, —CN or halogen;
$R^4$ is H; and
p is 0, 1 or 2.

Embodiment C. A compound of Embodiment B wherein
each $R^5$ is independently $C_1$-$C_4$ alkyl, $C_1$-$C_4$ haloalkyl, halogen, —CN, $C_1$-$C_4$ alkoxy or $C_1$-$C_4$ haloalkoxy;
each $R^6$ is independently $C_1$-$C_4$ haloalkyl, halogen, —CN or $C_1$-$C_4$ haloalkoxy;
$R^7$ is phenyl optionally substituted with one to three substituents independently selected from $R^9$; or
$R^7$ is

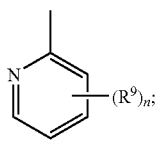

each $R^9$ is independently $C_1$-$C_4$ alkyl, $C_1$-$C_4$ haloalkyl, halogen or —CN;
$R^8$ is $CH_2CF_3$ or $CHF_2$; and
n is 0, 1 or 2.

Embodiment D. A compound of Embodiment C wherein
each $R^6$ is independently halogen, $OCH_2CF_3$, $OCHF_2$ or $CF_3$; and
each $R^9$ is independently $CH_3$, $CF_3$, —CN or halogen.

Embodiment E. A compound of Embodiment D wherein J is a heterocyclic ring selected from the group consisting of J-1, J-2 and J-3.

Embodiment F. A compound of Embodiment E wherein
$R^1$ is $CH_3$, F, Cl, Br or I;
$R^2$ is H, $CH_3$, $CF_3$, —CN, F, Cl, Br or I; and
each $R^6$ is independently Cl, Br, $OCH_2CF_3$ or $CF_3$.

Embodiment G. A compound of Embodiment F wherein
$R^3$ is —C(=O)C(=O)OH.

Embodiment H. A compound of Embodiment F wherein
$R^3$ is —C(=O)C(=O)N$R^{14}R^{15}$.

Specific embodiments include compounds of Formula 1 selected from the group consisting of:
1-(3-chloro-2-pyridinyl)-N-[2-methyl-6-[2-[(1-methylethyl)amino]-2-oxoethyl]phenyl]-3-(trifluoromethyl)-1H-pyrazole-5-carboxamide;
1-(3-chloro-2-pyridinyl)-N-[2-[(diethylamino)oxoacetyl]-4,6-dimethylphenyl]-3-(trifluoromethyl)-1H-pyrazole-5-carboxamide;
1-(3-chloro-2-pyridinyl)-N-[2-[(1Z)-2-(diethylamino)-1-(hydroxyimino)-2-oxoethyl]-4,6-dimethylphenyl]-3-(trifluoromethyl)-1H-pyrazole-5-carboxamide;
2-[[[3-bromo-1-(3-chloro-2-pyridinyl)-1H-pyrazol-5-yl]carbonyl]amino]-5-chloro-3-methyl-α-oxobenzeneacetic acid;
1-[[3-bromo-1-(3-chloro-2-pyridinyl)-1H-pyrazol-5-yl]carbonyl]-5-chloro-7-methyl-1H-indole-2,3-dione;
3-bromo-N-[4-chloro-2-methyl-6-[(1E)-2-(methylamino)-1-(methylimino)-2-oxoethyl]phenyl]-1-(3-chloro-2-pyridinyl)-1H-pyrazole-5-carboxamide; and
3-bromo-N-[4-chloro-2-methyl-6-[(methylamino)oxoacetyl]phenyl]-1-(3-chloro-2-pyridinyl)-1H-pyrazole-5-carboxamide.

Further specific embodiments include any combination of the compounds of Formula 1 selected from the group immediately above.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said composition optionally further comprising at least one additional biologically active compound or agent.

Also noteworthy as embodiments of the present invention are compositions for controlling an invertebrate pest comprising a biologically effective amount of a compound of any of the preceding Embodiments, as well as any other embodiments described herein, and any combinations thereof, and at least one additional component selected from the group consisting of a surfactant, a solid diluent and a liquid diluent, said composition optionally further comprising a biologically effective amount of at least one additional biologically active compound or agent. Embodiments of the invention further include methods for controlling an invertebrate pest comprising contacting the invertebrate pest or its environment with a biologically effective amount of a compound of any of the preceding Embodiments, as well as any other embodiments described herein, and any combinations thereof (e.g., as a composition described herein).

Embodiments of the invention also include a composition comprising a compound of any of the preceding Embodiments, as well as any other embodiments described herein, and any combinations thereof, in the form of a soil drench liquid formulation. Embodiments of the invention further include methods for controlling an invertebrate pest comprising contacting the soil with a liquid composition as a soil drench comprising a biologically effective amount of a compound of any of the preceding Embodiments, as well as any other embodiments described herein, and any combinations thereof.

Embodiments of the invention also include a spray composition for controlling an invertebrate pest comprising a biologically effective amount of a compound of any of the preceding Embodiments, as well as any other embodiments described herein, and any combinations thereof and a propellant. Embodiments of the invention further include a bait composition for controlling an invertebrate pest comprising a biologically effective amount of a compound of any of the preceding Embodiments, as well as any other embodiments described herein, and any combinations thereof, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Compounds of Formula 1 can be prepared by one or more of the following methods and variations as described in Schemes 1-12. The definitions of X, J, B, L, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in the compounds of Formulae 1-11 below are as defined above in the Summary of the Invention unless indicated otherwise. Formulae 1a-1j are subsets of Formula 1, and Formulae 9a-9c are subsets of Formula 9.

Compounds of Formula 1a, wherein B is $NR^{13}$, $NOR^{13}$ or $NNR^{14}R^{15}$, can be prepared by the reaction of compounds of Formula 1c with corresponding amines, alkoxylamines or hydrazines of Formula 2 as outlined in Scheme 1. This reaction can be run neat or in a variety of suitable solvents including water, methanol, ethanol, acetonitrile or tetrahydrofuran with optimum temperatures ranging from room temperature to the reflux temperature of the solvent. The general reaction of ketones with amines to produce imines, oximes and hydrazones is well documented in the chemical literature. For examples of this type see A. Franke, *Liebigs Ann. Chem.* 1982, (4), 794-804. In a subsequent step, amides of Formula 1a can be converted to thioamides of Formula 1b using a variety of standard thio transfer reagents including phosphorus pentasulfide and 2,4-bis-(4-methoxyphenyl)-1,3-dithia-2,4-diphosphetane 2,4-disulfide (Lawesson's reagent). Compounds of Formula 1b, where X is S and B is O, can be prepared from imines of Formula 1b, where X is S and B is $NR^{13}$, by hydrolysis of the imine group using aqueous acid such as hydrochloric acid, sulfuric acid or acetic acid, optionally with co-solvent such as methanol or tetrahydrofuran.

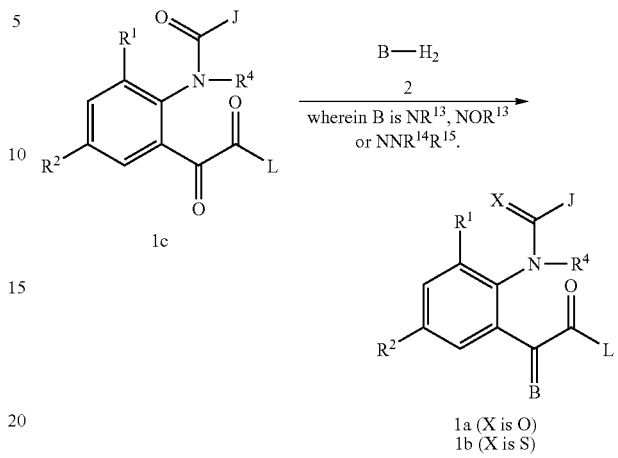

Scheme 1

Compounds of Formulae 1d and 1e can be prepared by the reaction of compounds of Formulae 1g or 1h with aqueous base, such as potassium carbonate or sodium hydroxide, or with an amine of Formula 3 as outlined in Scheme 2. When $R^{15}$ is H, it is possible to obtain compounds of Formula 1f wherein $R^3$ is $-C(=NR^{14})C(=O)NHR^{14}$ directly. Imines of Formula 1f can be converted to compounds of Formula 1e wherein $R^4$ and $R^{15}$ are H by treatment with aqueous acids such as hydrochloric acid, sulfuric acid or acetic acid, optionally with co-solvent such as methanol or tetrahydrofuran.

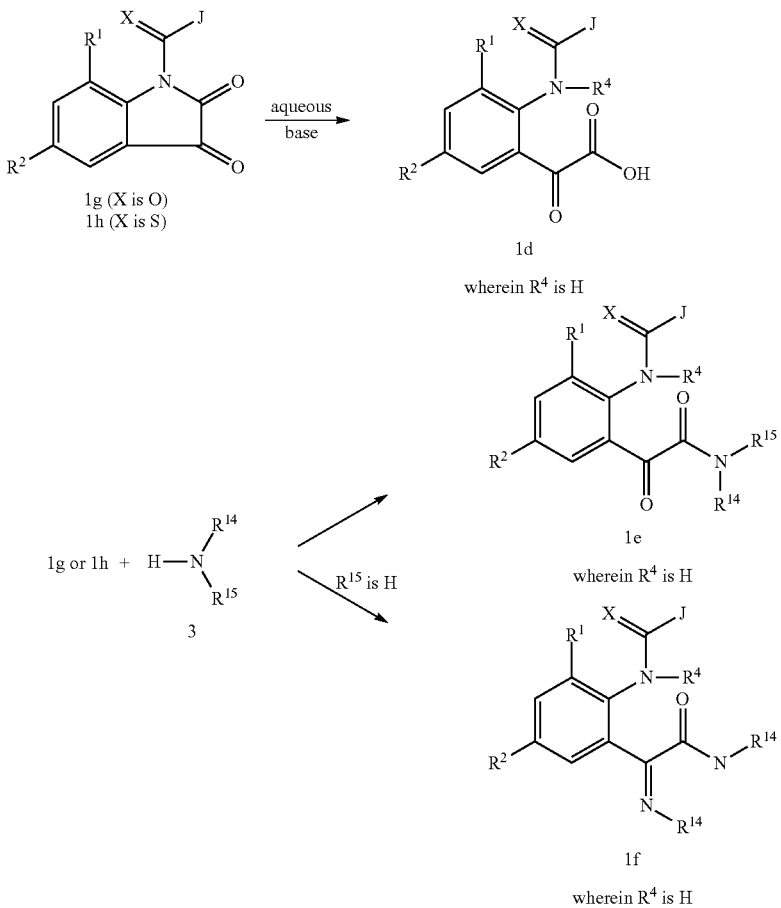

Scheme 2

This reaction can be run neat or in a variety of suitable solvents including methanol, ethanol, acetonitrile or tetrahydrofuran with optimum temperatures ranging from room temperature to the reflux temperature of the solvent. For examples of reactions of isatins with amines see A. Franke, *Liebigs Ann. Chem.* 1982, (4), 794-804. For examples of reactions of isatins with aqueous base see B. A. Johnson and K. Undheim, *Acta Chemica Scand., Series B* 1984, B38(2), 109-112. Preparation of compounds of Formulae 1d, 1e or 1f, wherein $R^4$ is other than H (e.g., alkyl, alkylcarbonyl, etc.), can be accomplished by standard alkylation or acylation of the amide by treatment with a base (such as sodium hydride in N,N-dimethylformamide) and the alkylating or acylating reagent.

Compounds of Formula 1g can be prepared by acylation of isatins of Formula 4 with acid chlorides or mixed anhydrides of Formula 5 in the presence of a base such as triethylamine, pyridine or 3-picoline as outlined in Scheme 3. This reaction can be run in a variety of suitable solvents including acetonitrile, dichloromethane, chloroform or tetrahydrofuran with optimum temperatures ranging from 0° C. to the reflux temperature of the solvent. The acylation of isatins is well documented in the chemical literature. For example see T. L. Jacobs et al., *Organic Syntheses* 1948, 28, 70-2 and A. Ferranti et al., *Arch. Pharm.* 1985, 318(5) 415-421. In a subsequent step, amides of Formula 1g can be converted to thioamides of Formula 1h using a variety of standard thio transfer reagents including phosphorus pentasulfide and Lawesson's reagent.

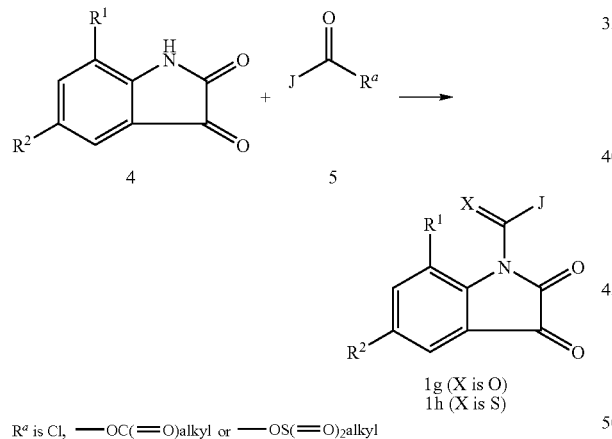

Isatins of Formula 4 are well known and can be prepared from aniline derivatives following literature procedures such as those described by F. D. Popp, *Adv. Heterocycl. Chem.* 1975, 18, 1-58 and J. F. M. Da Silva et al., *Journal of the Brazilian Chemical Society* 2001, 12(3), 273-324.

The acid chlorides of Formula 5 are available from the corresponding acids of Formula 6 by known methods such as chlorination with thionyl chloride or oxalyl chloride as outlined in Scheme 4. The mixed anhydrides can be prepared in situ from the corresponding acids by treatment with an alkyl chloroformate or alkylsulfonyl chloride in the presence of a base such as triethylamine, pyridine or 3-picoline by well known methods. The acids of Formula 6 can be prepared as disclosed in WO 03/016283 and U.S. Pat. No. 6,747,047.

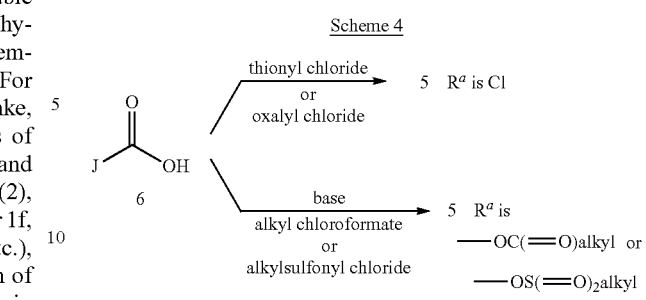

Alternatively compounds of Formula 1e (i.e. Formula 1 wherein $R^3$ is —C(=O)C(=O)—NR$^{14}$R$^{15}$) can be prepared by acylation of anilines of Formula 7 with acid chlorides or other activated derivatives of carboxylic acids of Formula 6 in the presence of base such as triethylamine, pyridine or 3-picoline as outlined in Scheme 5. This reaction can be run in a variety of suitable solvents including acetonitrile, dichloromethane, chloroform or tetrahydrofuran with optimum temperatures ranging from 0° C. to the reflux temperature of the solvent.

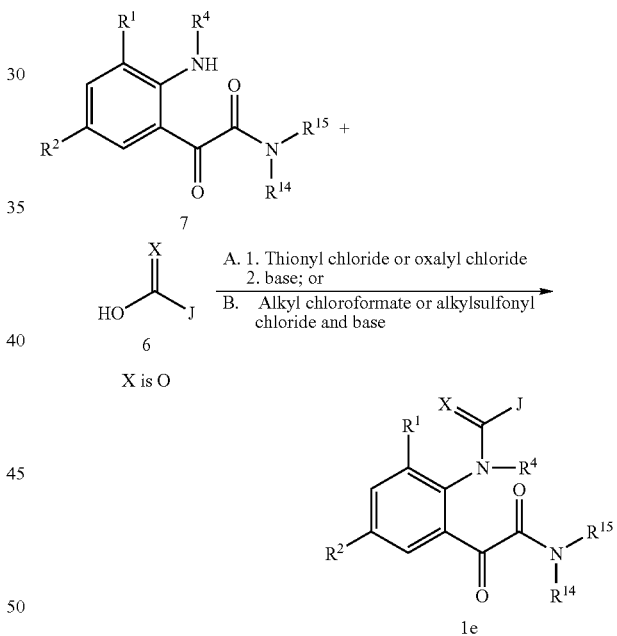

Anilines of Formula 7, wherein $R^4$ is H, can be prepared by reaction of isatins of Formula 4 with amines of Formula 3 as outlined in Scheme 6.

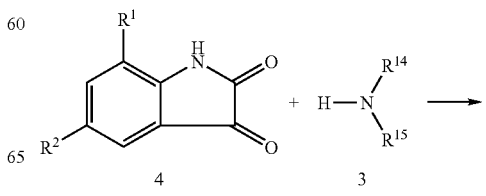

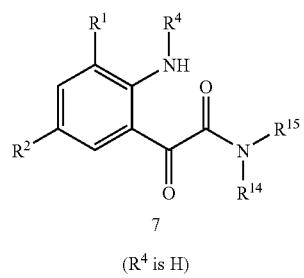

7

($R^4$ is H)

This reaction can be run neat or in a variety of suitable solvents including water, methanol, ethanol, acetonitrile or tetrahydrofuran with optimum temperatures ranging from room temperature to the reflux temperature of the solvent. For examples of this procedure see J. Hlavac et al., *J. Het. Chem.*, 2004, 41(4), 633-636 and J. Bergman et al. *Acta Chemica Scand.*, 1997, 51(6/7), 753-759.

Compounds of Formula 1j (i.e. Formula 1 wherein $R^3$ is —C($R^{11}R^{12}$)C(=O)L) can be prepared by acylation of anilines of Formula 8 with acid chlorides of Formula 5 in the presence of a base such as triethylamine, pyridine or 3-picoline as outlined in Scheme 7. This reaction can be run in a variety of suitable solvents including acetonitrile, dichloromethane, chloroform or tetrahydrofuran with optimum temperatures ranging from 0° C. to the reflux temperature of the solvent.

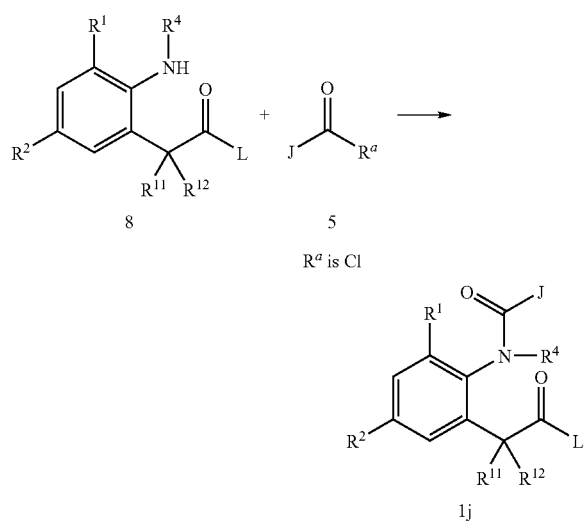

Anilines of Formula 8 wherein $R^4$ is H can be prepared by reduction of nitro compounds of Formula 9 as outlined in Scheme 8. A variety of methods can be used for this transformation including catalytic hydrogenation, or treatment with iron in acetic acid or stannic chloride.

Compounds of Formula 8 wherein $R^4$ is alkyl, alkenyl, alkynyl or substituted derivatives thereof can be prepared by treatment of the aniline 8 wherein $R^4$ is H with an appropriate aldehyde in the presence of a reducing agent such as sodium cyanoborohydride.

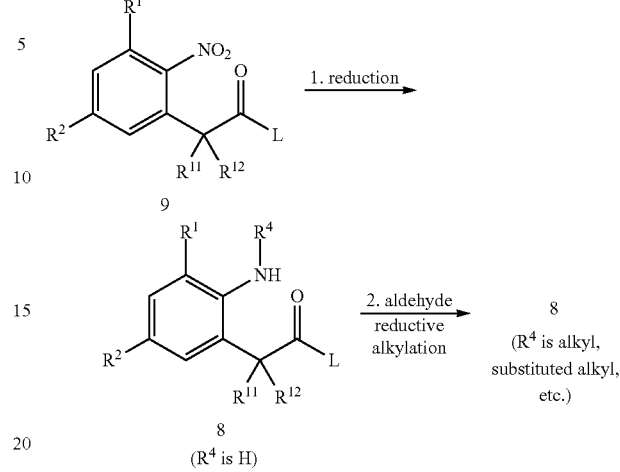

Nitro compounds of Formula 9 wherein $R^{11}$ and $R^{12}$ are independently $C_1$-$C_6$ alkyl, $C_2$-$C_6$ alkenyl, $C_2$-$C_6$ alkynyl or $C_3$-$C_6$ cycloalkyl can be prepared by alkylation of nitro compounds of Formula 9a with the appropriate alkyl (or alkenyl, alkynyl or cycloalkyl) halides of Formulae 10a and 10b as outlined in Scheme 9. Particularly useful halides are bromides and iodides. This reaction can be run with a variety of bases including potassium t-butoxide, potassium carbonate and sodium hydride in a variety of suitable solvents including acetonitrile, ether or tetrahydrofuran. Either the mono or dialkylation products can be obtained by adjusting the stoichiometry of the reagents. For reactions of this type see T. J. Greshock and R. L. Funk, *J. Amer. Chem. Soc.*, 2002, 124(5), 754-755, R. A. Bunce et al., *J. Org. Chem.*, 2001, 66(8), 2822-2827 and M. Somei et al., *Heterocycles*, 1985, 23(5), 1101-1106.

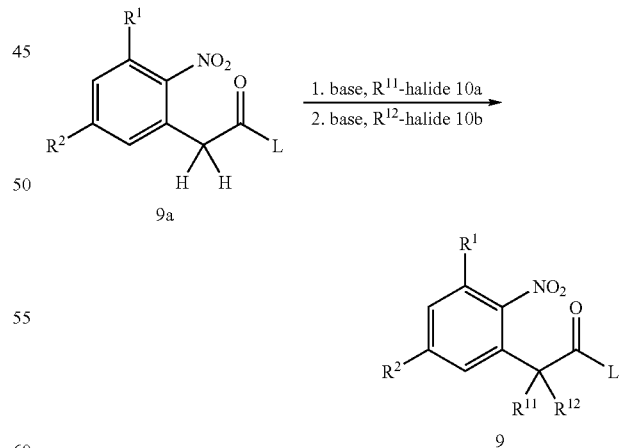

wherein $R^{11}$ and $R^{12}$ are independently $C_1$-$C_6$ alkyl, $C_2$-$C_6$ alkenyl, $C_2$-$C_6$ alkynyl or $C_3$-$C_6$ cycloalkyl Nitro compounds of Formula 9 wherein $R^{11}$ and $R^{12}$ are independently halogen can be prepared by halogenation of nitro compounds of Formula 9a as outlined in Scheme 10.

Scheme 10

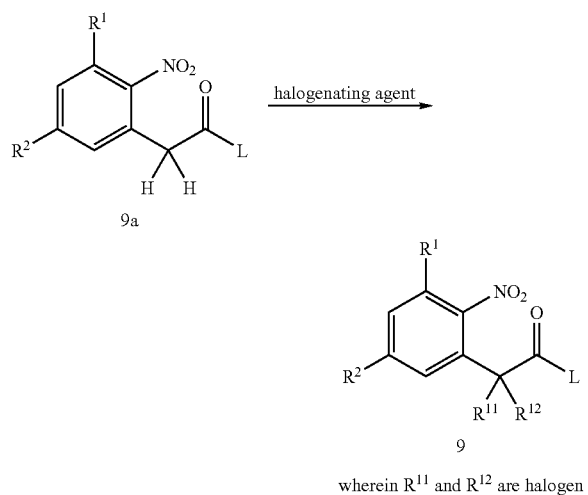

wherein R¹¹ and R¹² are halogen

A variety of halogenating reagents can be employed such as a N-halosuccinimide, bromine (for $R^{11}$ is bromine), chlorine (for $R^{11}$ is chlorine) or Selectfluor™ (i.e. 1-chloromethyl-4-fluoro-1,4-diazoniabicyclo[2,2,2]octane bis(tetrafluoroborate)) (for $R^{11}$ is fluorine) in a variety of suitable solvents including carbon tetrachloride, chloroform, acetonitrile or tetrahydrofuran with optimum temperatures ranging from room temperature to the reflux temperature of the solvent. For an example see K. Schaper et al., *Eur. J. Org. Chem.*, 2002, (6), 1037-1046.

Nitro compounds of Formula 9b can be prepared from nitro compounds of Formula 9c by amination with amines of Formula 3 as outlined in Scheme 11. The reaction can be performed by a variety of standard methods such as forming the acid chloride of the compound of Formula 9c and then reacting with the amine of Formula 3 or treating the compound of Formula 9c with a variety of coupling reagents such as 1,3-dicyclohexylcarbodiimide or 1-(3-dimethylaminopropyl)-3-ethylcarbodiimide hydrochloride in the presence of the amine of Formula 3.

Scheme 11

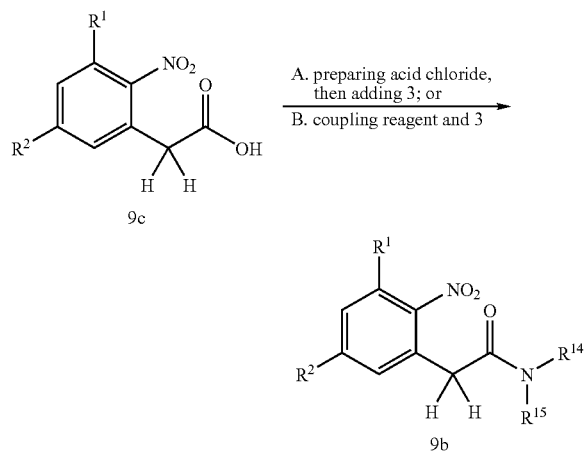

Nitro compounds of Formula 9c can be prepared by acylation of ortho-nitrotoluene compounds of Formula 11 with dimethyl or diethyl oxalate in the presence of base, followed by oxidation with basic hydrogen peroxide as outlined in Scheme 12. An example of this procedure can be found in H. Rapoport et al., *J. Org. Chem.*, 1954, 77, 670-675. ortho-Nitro toluene compounds of Formula 11 are commercially available or are known in the art.

Scheme 12

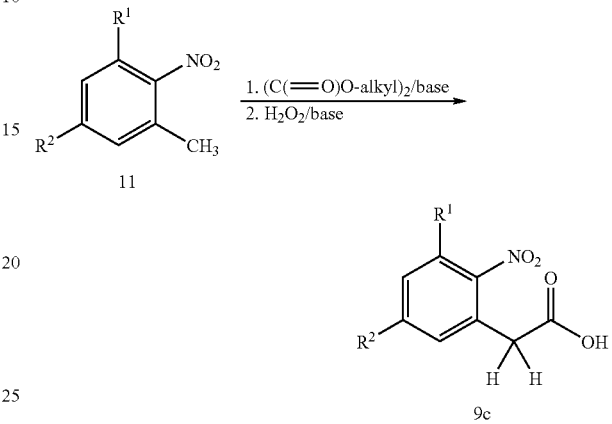

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. ¹H NMR spectra are reported in ppm downfield from tetramethylsilane; s means singlet, d means doublet, t means triplet, q means quartet, m means multiplet, dd means doublet of doublets, dt means doublet of triplets, br s means broad singlet.

EXAMPLE 1

Preparation of 1-(3-chloro-2-pyridinyl)-N-[2-methyl-6-[2-[(1-methylethyl)amino]-2-oxoethyl]phenyl]-3-(trifluoromethyl)-1H-pyrazole-5-carboxamide Step A: Preparation of 3-methyl-N-(1-methylethyl)-2-nitrobenzeneacetamide To a slurry of 3-methyl-2-nitrobenzeneacetic acid (prepared by the method of H. Rapoport et al., *J. Org. Chem.*, 1954, 77, 670-675 from 1,3-dimethyl-2-nitrobenzene, 0.70 g, 3.6 mmol) in 10 mL of dichloromethane was added oxalyl chloride (0.41 mL, 4.7 mmol) and two drops of N,N-dimethylformamide. The reaction mixture was stirred for 20 minutes, resulting in a solution. The volatiles were removed with a rotary evaporator. The residue was dissolved in 10 mL of dichloromethane. Half of this material was added dropwise at 0° C. to isopropylamine (1 mL) in 5 mL of dichloromethane. The reaction mixture was stirred overnight at room temperature. Saturated sodium bicarbonate solution was added, and the reaction mixture was passed through a Celite® diatomaceous filter aid cartridge. The solvent was removed with a rotary evaporator to afford the title compound as an orange solid (0.40 g).

$^1$H NMR (CDCl$_3$) δ 7.35 (m, 2H), 7.23 (d, 1H), 5.48 (br s, 1H), 4.03 (m, 1H), 3.44 (s, 2H), 2.36 (s, 3H), 1.10 (d, 6H).

Step B: Preparation of 2-amino-3-methyl-N-(1-methylethyl)benzeneacetamide

To 3-methyl-N-(1-methylethyl)-2-nitrobenzeneacetamide (i.e. the title product of Step A) (0.40 g, 1.7 mmol) and 10% palladium on carbon (0.13 g) was added 20 mL of ethanol. The reaction mixture was placed under a balloon of nitrogen overnight. Then the reaction mixture was filtered through Celite® diatomaceous filter aid. The solvent was removed with a rotary evaporator to afford the title compound as a tan solid (0.29 g).

$^1$H NMR (CDCl$_3$) δ 7.00 (d, 1H), 6.90 (d, 1H), 6.66 (dd, 1H), 5.40 (br s, 1H), 4.16 (br s, 2H) 4.04 (m, 1H), 3.44 (s, 2H), 2.19 (s, 3H), 1.08 (d, 6H).

Step C: Preparation of 1-(3-chloro-2-pyridinyl)-N-[2-methyl-6-[2-[(1-methylethyl)amino]-2-oxoethyl]phenyl]-3-(trifluoromethyl)-1H-pyrazole-5-carboxamide To a slurry of 1-(3-chloro-2-pyridinyl)-3-(trifluoromethyl)-1H-pyrazole-5-carboxylic acid (for preparation see WO 02/48115, 0.19 g, 0.66 mmol) in 10 mL of dichloromethane was added oxalyl chloride (0.087 mL, 1.0 mmol) and two drops of N,N-dimethylformamide. The reaction mixture was stirred for 15 minutes, resulting in a solution. The volatiles were removed with a rotary evaporator. The residue was dissolved in 10 mL of tetrahydrofuran, and the solution was added dropwise at 0° C. to 2-amino-3-methyl-N-(1-methylethyl)-benzeneacetamide (i.e. the title product of Step B) (0.14 g, 0.66 mmol), N,N-diisopropyl-ethylamine, (0.23 mL, 1.3 mmol) and 4-(dimethylamino)pyridine (5 mg) in 5 mL of tetrahydrofuran. The reaction mixture was stirred overnight at room temperature. Dichloromethane was added and the mixture was washed with water and dried (sodium sulfate). The solvent was removed with a rotary evaporator. The residue was purified by MPLC (40→60% ethyl acetate in hexanes as eluant) to afford the title compound plus an impurity. The material was purified further by MPLC (20→30% ethyl acetate in 1-chlorobutane as eluant) to afford the title product, a compound of the present invention, as a white solid (0.12 g), m.p. 206-207° C.

$^1$H NMR (CDCl$_3$) δ 10.78 (br s, 1H), 8.48 (dd, 1H), 8.70 (dd, 1H), 7.40 (dd, 1H), 7.34 (s, 3H), 7.11 (m, 2H), 6.97 (m, 1H), 5.65 (br d, 1H), 4.05 (m, 1H), 3.44 (s, 2H), 2.22 (s, 3H), 1.15 (d, 6H).

EXAMPLE 2

Preparation of 1-(3-chloro-2-pyridinyl)-N-[2-[(diethylamino)oxoacetyl]-4,6-dimethylphenyl]-3-(trifluoromethyl)-1H-pyrazole-5-carboxamide Step A: Preparation of 2-amino-N N-diethyl-3,5-dimethyl-α-oxobenzeneacetamide A mixture of 5,7-dimethyl-1H-indole-2,3-dione (1.0 g, 5.7 mmol), diethylamine (2.9 mL, 29 mmol), water (1.7 mL) and methanol (5.7 mL) was heated at 60° C. for 15 h. The resulting mixture was diluted with acetonitrile (100 mL) and concentrated onto silica gel (3g). The resulting material was purified by MPLC on a silica gel column eluted with a gradient of 30% to 50% ethyl acetate in hexanes to afford 1.31 g of the title compound as a tacky solid.

$^1$H NMR (CDCl$_3$) δ 7.11 (d, 1H), 7.08 (d, 1H), 6.25 (br s, 2H), 3.56 (q, 2H), 3.23 (q, 2H), 2.19 (s, 3H), 2.15 (s, 3H), 1.29 (t, 3H), 1.15 (t, 3H).

Step B: Preparation of 1-(3-chloro-2-pyridinyl)-N-[2-[(diethylamino)oxoacetyl]-4,6-dimethylphenyl]-3-(trifluoromethyl)-1H-pyrazole-5-carboxamide A suspension of 1-(3-chloro-2-pyridinyl)-3-(trifluoromethyl)-1H-pyrazole-5-carboxylic acid (1.5 g, 5.1 mmol) and dichloromethane (15 mL) was treated successively with oxalyl chloride (0.67 mL, 7.7 mmol) and N,N-dimethylformamide (1 drop) with stirring at 25° C. Gas evolution occurred over ca. 30 minutes and the mixture gradually became homogeneous. After stirring for 2 h at 25° C. the brown solution was concentrated, the residue was dissolved in 1,2-dichloroethane (20 mL) and the resulting solution was concentrated. The residue was dissolved in 1,2-dichloroethane (13 mL), and an aliquot (3.3 mL) of this solution was added to 2-amino-N,N-diethyl-3,5-dimethyl-α-oxobenzeneacetamide (i.e. the title product of Step A) (266 mg, 1.1 mmol). The resulting solution was cooled in an ice-water bath and treated with N,N-diisopropylethylamine (0.28 mL, 1.6 mmol). The resulting mixture was stirred at 25° C. for 15 h and then partitioned between ethyl acetate and 0.2N aqueous hydrochloric acid. The organic layer was washed with saturated aqueous sodium bicarbonate, dried (MgSO$_4$) and concentrated onto 1 g of silica gel. Flash chromatography of the residue on silica gel eluted with 50% ethyl acetate in hexanes gave 470 mg of the title product, a compound of the present invention, as a tacky solid.

$^1$H NMR (CDCl$_3$) δ 9.98 (br s, 1H), 8.48 (d, 1H), 7.85 (d, 1H), 7.43 (s, 1H), 7.43-7.39 (m, 1H), 7.33 (s, 1H), 7.29 (s, 1H), 3.50 (q, 2H), 3.18 (q, 2H), 2.33 (s, 3H), 2.19 (s, 3H), 1.24 (t, 3H), 1.11 (t, 3H).

EXAMPLE 3

Preparation of 1-(3-chloro-2-pyridinyl)-N-[2-[(1Z)-2-(diethylamino)-1-(hydroxyimino)-2-oxoethyl]-4,6-dimethylphenyl]-3-(trifluoromethyl)-1H-pyrazole-5-carboxamide A solution of hydroxylamine hydrochloride (50 mg, 0.71 mmol) in water (0.5 mL) was added to a solution of 1-(3-chloro-2-pyridinyl)-N-[2-[(diethylamino)oxoacetyl]-4,6-dimethylphenyl]-3-(trifluoromethyl)-1H-pyrazole-5-carboxamide (i.e. the title product of Example 2, 124 mg, 0.24 mmol) in ethanol (5 mL) at 25° C. The resulting mixture was treated with a solution of sodium acetate (200 mg) in water (2 mL). The resulting mixture was heated at reflux for 3 days and then cooled to 25° C., diluted with ethanol (30 mL) and concentrated onto silica gel (0.5 g). The residue was purified by flash chromatography on silica gel eluted with 35% ethyl acetate in hexanes to give 50 mg of the title product, a compound of the present invention, as a yellow glassy solid.

$^1$H NMR (CDCl$_3$) δ 9.64 (s, 1H), 8.40 (d, 1H), 7.83 (d, 1H), 7.39 (dd, 1H), 7.31 (s, 1H), 6.98 (s, 1H), 6.91 (s, 1H), 3.52 (q, 2H), 3.15 (q, 2H), 2.22 (s, 3H), 2.11 (s, 3H), 1.28-1.18 (m, 6H).

EXAMPLE 4

Preparation of 2-[[[3-bromo-1-(3-chloro-2-pyridinyl)-1H-pyrazol-5-yl]carbonyl]amino]-5-chloro-3-methyl-α-oxobenzeneacetic acid To a suspension of 3-bromo-1-(3-chloro-2-pyridinyl)-1H-pyrazole-5-carboxylic acid (see PCT Patent Publication WO 03/015519 for preparation) (97.6% purity, 3.25 g, 10.5 mmol) and 5-chloro-7-methylindoline-2,3-dione (K. Tsuji et al., Bioorg. Med. Chem. Letters, 2002, 12(17), pp 2427-2430) (1.96 g, 10.0 mmol) in dry acetonitrile (12 mL) was added 3-picoline (2.60 g, 28 mmol). The mixture was cooled to 0° C., and then methanesulfonyl chloride (1.48 g, 12.9 mmol) was added dropwise at 0-10° C. After stirring 5 minutes at this temperature, the mixture was warmed to room temperature for 2 hours. Then additional quantities of 3-picoline (0.37 g, 4.0 mmol) and methanesulfonyl chloride (0.24 g, 2.1 mmol) were added, and stirring was continued at room temperature for 3 hours. The mixture was cooled to 0° C., water (6 mL) was added dropwise, and stirring at 0-5° C. was continued for 1 hour. Then the mixture was filtered, and the solids were washed with 2:1 acetonitrile-water (3×3 mL), and dried under nitrogen to afford the 3-picoline salt of the title compound as a light green solid, 1.23 g.

The isolated solid was suspended in acetonitrile (3 mL) and 1N aqueous hydrochloric acid (3 mL) was added dropwise. The solids dissolved, and then a new precipitate formed. The mixture was stirred at room temperature for 1 hour, and the precipitate was filtered, washed with 1:1 acetonitrile-water (3×2 mL), and dried under nitrogen to afford the title product, a compound of the present invention, as an off-white solid, 0.27 g (5.6% yield), m.p. 139-142° C.

$^1$H NMR (DMSO-d$_6$) δ 2.22 (s, 3H), 7.29 (s, 1H), 7.58 (d, J=2.4 Hz, 1H), 7.61 (dd, J=8.2, 4.6 Hz, 1H), 7.71 (d, J=2.4 Hz, 1H), 8.17 (dd, J=8.2, 1.4 Hz, 1H), 8.49 (dd, J=4.6, 1.4 Hz, 1H), 10.57 (br s, 1H).

EXAMPLE 5

Preparation of 1-[[3-bromo-1-(3-chloro-2-pyridinyl)-1H-pyrazol-5-yl]carbonyl]-5-chloro-7-methyl-1H-indole-2,3-dione To a suspension of 3-bromo-1-(3-chloro-2-pyridinyl)-1H-pyrazole-5-carboxylic acid (see PCT Patent Publication WO 03/015519 for preparation) (97.6% purity, 13.02 g, 42 mmol) and 5-chloro-7-methylindoline-2,3-dione (K. Tsuji et al., Bioorg. Med. Chem. Letters, 2002, 12(17), pp 2427-2430) (7.82 g, 40 mmol) in dry acetonitrile (50 mL) was added 3-picoline (11.9 g, 127 mmol). The mixture was cooled to 0° C., and then methanesulfonyl chloride (6.87 g, 60 mmol) was added dropwise at 0-10° C. After stirring 5 minutes at this temperature, the mixture was warmed to room temperature for 20 hours. The precipitated solids were filtered, washed with acetonitrile (3×5 mL), and dried under nitrogen to afford the title product, a compound of the present invention, as a yellow powder, 14.90 g (77.6% yield), m.p. 173-177° C. (decomp.).

$^1$H NMR (CDCl$_3$) δ 2.16 (s, 3H), 7.14 (s, 1H), 7.38 (dd, J=8.1, 4.8 Hz, 1H), 7.53 (d, J=2.1 Hz, 1H), 7.60 (d, J=2.1 Hz, 1H), 7.89 (dd, J=8.1, 1.5 Hz, 1H), 8.39 (dd, J=4.8, 1.5 Hz, 1H). The NMR spectrum also showed that some 3-picoline salts were present in the crude product.

EXAMPLE 6

Preparation of 3-bromo-N-[4-chloro-2-methyl-6-[(1E)-2-(methylamino)-1-(methylimino)-2-oxoethyl]phenyl]-1-(3-chloro-2-pyridinyl)-1H-pyrazole-5-carboxamide A suspension of 1-[[3-bromo-1-(3-chloro-2-pyridinyl)-1H-pyrazol-5-yl]carbonyl]-5-chloro-7-methyl-1H-indole-2,3-dione (i.e. the crude product of Example 5) (4.80 g, 10 mmol) in acetonitrile (15 mL) was cooled to −10° C., and liquefied methylamine (0.35 g, 11 mmol) was added. The mixture was stirred for 1 hour at −10° C., then warmed to 0° C., and three more portions of liquefied methylamine (each 0.35 g, 11 mmol) were added periodically. Finally the reaction mass was filtered, and the solids were washed with acetonitrile (3×2 mL) and dried under nitrogen to afford the title product, a compound of the present invention, as off-white solids, 1.09 g. Almost immediately, more solids began to precipitate from the filtrate. These were filtered, washed with acetonitrile (3×2 mL), and dried under nitrogen to afford a second crop of the title product as light yellow crystals, 2.91 g, m.p. 230-234° C. (decomp.). The total isolated yield from both crops was 4.00 g (76.3%).

$^1$H NMR (CDCl$_3$) δ 2.08 (s, 3H), 2.92 (d, J=5.1 Hz, 1H), 3.11 (s, 3H), 6.85 (d, J=2.4 Hz, 1H), 7.05 (s, 1H), 7.21 (dd, J=2.4, 0.6 Hz, 1H), 7.36 (dd, J=8.0, 4.8 Hz, 1H), 7.64 (br quartet, J=5.1 Hz, 1H), 7.83 (dd, J=8.0, 1.5 Hz, 1H), 8.45 (dd, J=4.8, 1.5 Hz, 1H).

EXAMPLE 7

Preparation of 3-bromo-N-[4-chloro-2-methyl-6-[(methylamino)oxoacetyl]phenyl]-1-(3-chloro-2-pyridinyl)-1H-pyrazole-5-carboxamide To a suspension of 3-bromo-N-[4-chloro-2-methyl-6-[(1E)-2-(methylamino)-1-(methylimino)-2-oxoethyl]phenyl]-1-(3-chloro-2-pyridinyl)-1H-pyrazole-5-carboxamide (i.e. the product of Example 6) (0.52 g, 1.0 mmol) in acetonitrile (8 mL) was added 1N aqueous hydrochloric acid (2.0 mL, 2.0 mmol), and the mixture was stirred for 2 hours at room temperature. Then the mixture was filtered, and the solids were washed with 2:1 acetonitrile-water (3×1 mL), and dried under nitrogen to afford the title product, a compound of the present invention, as off-white solids, 0.42 g (83% yield), m.p. 246-247° C.

$^1$H NMR (DMSO-d$_6$) δ 2.22 (s, 3H), 2.62 (d, J=4.8 Hz, 1H), 7.28 (s, 1H), 7.52 (d, J=2.6 Hz, 1H), 7.61 (dd, J=8.1, 4.8 Hz, 1H), 7.65 (d, J=2.6 Hz, 1H), 8.17 (dd, J=8.1, 1.5 Hz, 1H), 8.50 (dd, J=4.8, 1.5 Hz, 1H), 8.57 (br quartet, J=4.8 Hz, 1H).

EXAMPLE 8

Alternative method for the preparation of 3-bromo-N-[4-chloro-2-methyl-6-[(methylamino)oxoacetyl]phenyl]-[1-(3-chloro-2-pyridinyl)-1H-pyrazole-5-carboxamide A suspension of 1-[[3-bromo-1-(3-chloro-2-pyridinyl)-1H-pyrazol-5-yl]carbonyl]-5-chloro-7-methyl-1H-indole-2,3-dione (i.e. the crude product of Example 5) (4.80 g, 10 mmol) in acetonitrile (18 mL) was cooled to −10° C. and liquefied methylamine (1.05 g, 34 mmol) was added. The mixture was stirred for 5 minutes at −10° C. and then for 1 hour at room temperature. Then the mixture was cooled to 0° C., 6N aqueous hydrochloric acid (6.0 mL, 36 mmol) was added dropwise at 0-10° C., and the mixture was stirred for 1 hour at 0° C. The mixture was then filtered, and the solids were washed with 3:1 acetonitrile-water $^1$H NMR (DMSO-$d_6$) δ 2.22 (s, 3H), 2.62 (d, J=4.8 Hz, 1H), 7.28 (s, 1H), 7.52 (d, J=2.6 (3×3 mL), then with acetonitrile (3×3 mL), and dried under nitrogen to afford the title product, a compound of the present invention, as off-white solids, 3.66 g (71.6% yield). Hz, 1H), 7.61 (dd, J=8.1, 4.8 Hz, 1H), 7.65 (d, J=2.6 Hz, 1H), 8.17 (dd, J=8.1, 1.5 Hz, 1H), 8.50 (dd, J=4.8, 1.5 Hz, 1H), 8.57 (br quartet, J=4.8 Hz, 1H).

By the procedures described herein together with methods known in the art, the following compounds of Tables 1 to 6 can be prepared. The following abbreviations are used in the Tables which follow: t means tertiary, i means iso, Me means methyl, Et means ethyl, Pr means propyl, i-Pr means isopropyl, Bu means butyl, Ph means phenyl, OMe means methoxy, CN means cyano, 3-Cl-2-Py means 3-chloro-2-pyridinyl.

TABLE 1

| $R^1$ | $R^2$ | $R^6$ | X | $R^{14}$ | $R^{15}$ | B |
|---|---|---|---|---|---|---|
| Me | Cl | CF$_3$ | CH | Me | H | O |
| Me | Cl | Br | CH | Me | H | O |
| Me | Cl | Cl | CH | Me | H | O |
| Me | Br | CF$_3$ | CH | Me | H | O |
| Me | Br | Br | CH | Me | H | O |
| Me | Br | Cl | CH | Me | H | O |
| Me | CN | CF$_3$ | CH | Me | H | O |
| Me | CN | Br | CH | Me | H | O |
| Me | CN | Cl | CH | Me | H | O |
| Cl | Cl | CF$_3$ | CH | Me | H | O |
| Cl | Cl | Br | CH | Me | H | O |
| Cl | Cl | Cl | CH | Me | H | O |
| Br | Br | CF$_3$ | CH | Me | H | O |
| Br | Br | Br | CH | Me | H | O |
| Br | Br | Cl | CH | Me | H | O |
| Me | Cl | CF$_3$ | N | Me | H | O |
| Me | Cl | Br | N | Me | H | O |
| Me | Cl | Cl | N | Me | H | O |
| Me | Br | CF$_3$ | N | Me | H | O |
| Me | Br | Br | N | Me | H | O |
| Me | Br | Cl | N | Me | H | O |
| Me | CN | CF$_3$ | N | Me | H | O |
| Me | CN | Br | N | Me | H | O |
| Me | CN | Cl | N | Me | H | O |
| Cl | Cl | CF$_3$ | N | Me | H | O |
| Cl | Cl | Br | N | Me | H | O |
| Cl | Cl | Cl | N | Me | H | O |
| Br | Br | CF$_3$ | N | Me | H | O |
| Br | Br | Br | N | Me | H | O |
| Br | Br | Cl | N | Me | H | O |
| Me | Cl | CF$_3$ | CH | Et | H | O |
| Me | Cl | Br | CH | Et | H | O |
| Me | Cl | Cl | CH | Et | H | O |
| Me | Br | CF$_3$ | CH | Et | H | O |
| Me | Br | Br | CH | Et | H | O |
| Me | Br | Cl | CH | Et | H | O |
| Me | CN | CF$_3$ | CH | Et | H | O |
| Me | CN | Br | CH | Et | H | O |
| Me | CN | Cl | CH | Et | H | O |
| Cl | Cl | CF$_3$ | CH | Et | H | O |
| Cl | Cl | Br | CH | Et | H | O |
| Cl | Cl | Cl | CH | Et | H | O |
| Br | Br | CF$_3$ | CH | Et | H | O |
| Br | Br | Br | CH | Et | H | O |
| Br | Br | Cl | CH | Et | H | O |
| Me | Cl | CF$_3$ | N | Et | H | O |
| Me | Cl | Br | N | Et | H | O |
| Me | Cl | Cl | N | Et | H | O |
| Me | Br | CF$_3$ | N | Et | H | O |
| Me | Br | Br | N | Et | H | O |
| Me | Br | Cl | N | Et | H | O |
| Me | CN | CF$_3$ | N | Et | H | O |
| Me | CN | Br | N | Et | H | O |
| Me | CN | Cl | N | Et | H | O |
| Cl | Cl | CF$_3$ | N | Et | H | O |
| Cl | Cl | Br | N | Et | H | O |
| Cl | Cl | Cl | N | Et | H | O |
| Br | Br | CF$_3$ | N | Et | H | O |
| Br | Br | Br | N | Et | H | O |
| Br | Br | Cl | N | Et | H | O |
| Me | Cl | CF$_3$ | CH | i-Pr | H | O |
| Me | Cl | Br | CH | i-Pr | H | O |
| Me | Cl | Cl | CH | i-Pr | H | O |
| Me | Br | CF$_3$ | CH | i-Pr | H | O |
| Me | Br | Br | CH | i-Pr | H | O |

TABLE 1-continued

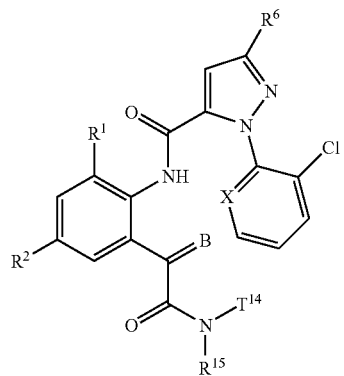

| R¹ | R² | R⁶ | X | R¹⁴ | R¹⁵ | B |
|---|---|---|---|---|---|---|
| Me | Br | Cl | CH | i-Pr | H | O |
| Me | CN | CF₃ | CH | i-Pr | H | O |
| Me | CN | Br | CH | i-Pr | H | O |
| Me | CN | Cl | CH | i-Pr | H | O |
| Cl | Cl | CF₃ | CH | i-Pr | H | O |
| Cl | Cl | Br | CH | i-Pr | H | O |
| Cl | Cl | Cl | CH | i-Pr | H | O |
| Br | Br | CF₃ | CH | i-Pr | H | O |
| Br | Br | Br | CH | i-Pr | H | O |
| Br | Br | Cl | CH | i-Pr | H | O |
| Me | Cl | CF₃ | N | i-Pr | H | O |
| Me | Cl | Br | N | i-Pr | H | O |
| Me | Cl | Cl | N | i-Pr | H | O |
| Me | Br | CF₃ | N | i-Pr | H | O |
| Me | Br | Br | N | i-Pr | H | O |
| Me | Br | Cl | N | i-Pr | H | O |
| Me | CN | CF₃ | N | i-Pr | H | O |
| Me | CN | Br | N | i-Pr | H | O |
| Me | CN | Cl | N | i-Pr | H | O |
| Cl | Cl | CF₃ | N | i-Pr | H | O |
| Cl | Cl | Br | N | i-Pr | H | O |
| Cl | Cl | Cl | N | i-Pr | H | O |
| Br | Br | CF₃ | N | i-Pr | H | O |
| Br | Br | Br | N | i-Pr | H | O |
| Br | Br | Cl | N | i-Pr | H | O |
| Me | Cl | CF₃ | CH | t-Bu | H | O |
| Me | Cl | Br | CH | t-Bu | H | O |
| Me | Cl | Cl | CH | t-Bu | H | O |
| Me | Br | CF₃ | CH | t-Bu | H | O |
| Me | Br | Br | CH | t-Bu | H | O |
| Me | Br | Cl | CH | t-Bu | H | O |
| Me | CN | CF₃ | CH | t-Bu | H | O |
| Me | CN | Br | CH | t-Bu | H | O |
| Me | CN | Cl | CH | t-Bu | H | O |
| Cl | Cl | CF₃ | CH | t-Bu | H | O |
| Cl | Cl | Br | CH | t-Bu | H | O |
| Cl | Cl | Cl | CH | t-Bu | H | O |
| Br | Br | CF₃ | CH | t-Bu | H | O |
| Br | Br | Br | CH | t-Bu | H | O |
| Br | Br | Cl | CH | t-Bu | H | O |
| Me | Cl | CF₃ | N | t-Bu | H | O |
| Me | Cl | Br | N | t-Bu | H | O |
| Me | Cl | Cl | N | t-Bu | H | O |
| Me | Br | CF₃ | N | t-Bu | H | O |
| Me | Br | Br | N | t-Bu | H | O |
| Me | Br | Cl | N | t-Bu | H | O |
| Me | CN | CF₃ | N | t-Bu | H | O |
| Me | CN | Br | N | t-Bu | H | O |
| Me | CN | Cl | N | t-Bu | H | O |
| Cl | Cl | CF₃ | N | t-Bu | H | O |
| Cl | Cl | Br | N | t-Bu | H | O |
| Cl | Cl | Cl | N | t-Bu | H | O |
| Br | Br | CF₃ | N | t-Bu | H | O |
| Br | Br | Br | N | t-Bu | H | O |
| Br | Br | Cl | N | t-Bu | H | O |
| Me | Cl | CF₃ | CH | Me | Me | O |
| Me | Cl | Br | CH | Me | Me | O |
| Me | Cl | Cl | CH | Me | Me | O |
| Me | Br | CF₃ | CH | Me | Me | O |

TABLE 1-continued

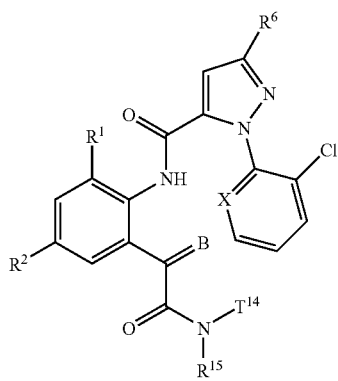

| R¹ | R² | R⁶ | X | R¹⁴ | R¹⁵ | B |
|---|---|---|---|---|---|---|
| Me | Br | Br | CH | Me | Me | O |
| Me | Br | Cl | CH | Me | Me | O |
| Me | CN | CF₃ | CH | Me | Me | O |
| Me | CN | Br | CH | Me | Me | O |
| Me | CN | Cl | CH | Me | Me | O |
| Cl | Cl | CF₃ | CH | Me | Me | O |
| Cl | Cl | Br | CH | Me | Me | O |
| Cl | Cl | Cl | CH | Me | Me | O |
| Br | Br | CF₃ | CH | Me | Me | O |
| Br | Br | Br | CH | Me | Me | O |
| Br | Br | Cl | CH | Me | Me | O |
| Me | Cl | CF₃ | N | Me | Me | O |
| Me | Cl | Br | N | Me | Me | O |
| Me | Cl | Cl | N | Me | Me | O |
| Me | Br | CF₃ | N | Me | Me | O |
| Me | Br | Br | N | Me | Me | O |
| Me | Br | Cl | N | Me | Me | O |
| Me | CN | CF₃ | N | Me | Me | O |
| Me | CN | Br | N | Me | Me | O |
| Me | CN | Cl | N | Me | Me | O |
| Cl | Cl | CF₃ | N | Me | Me | O |
| Cl | Cl | Br | N | Me | Me | O |
| Cl | Cl | Cl | N | Me | Me | O |
| Br | Br | CF₃ | N | Me | Me | O |
| Br | Br | Br | N | Me | Me | O |
| Br | Br | Cl | N | Me | Me | O |
| Me | Cl | CF₃ | N | Me | H | NMe |
| Me | Cl | Br | N | Me | H | NMe |
| Me | Cl | Cl | N | Me | H | NMe |
| Me | Br | CF₃ | N | Me | H | NMe |
| Me | Br | Br | N | Me | H | NMe |
| Me | Br | Cl | N | Me | H | NMe |
| Me | CN | CF₃ | N | Me | H | NMe |
| Me | CN | Br | N | Me | H | NMe |
| Me | CN | Cl | N | Me | H | NMe |
| Me | Cl | CF₃ | N | Me | H | NOMe |
| Me | Cl | Br | N | Me | H | NOMe |
| Me | Cl | Cl | N | Me | H | NOMe |
| Me | Br | CF₃ | N | Me | H | NOMe |
| Me | Br | Br | N | Me | H | NOMe |
| Me | Br | Cl | N | Me | H | NOMe |
| Me | CN | CF₃ | N | Me | H | NOMe |
| Me | CN | Br | N | Me | H | NOMe |
| Me | CN | Cl | N | Me | H | NOMe |
| Me | Cl | CF₃ | N | Me | H | NNMe₂ |
| Me | Cl | Br | N | Me | H | NNMe₂ |
| Me | Cl | Cl | N | Me | H | NNMe₂ |
| Me | Br | CF₃ | N | Me | H | NNMe₂ |
| Me | Br | Br | N | Me | H | NNMe₂ |
| Me | Br | Cl | N | Me | H | NNMe₂ |
| Me | CN | CF₃ | N | Me | H | NNMe₂ |
| Me | CN | Br | N | Me | H | NNMe₂ |
| Me | CN | Cl | N | Me | H | NNMe₂ |

TABLE 2

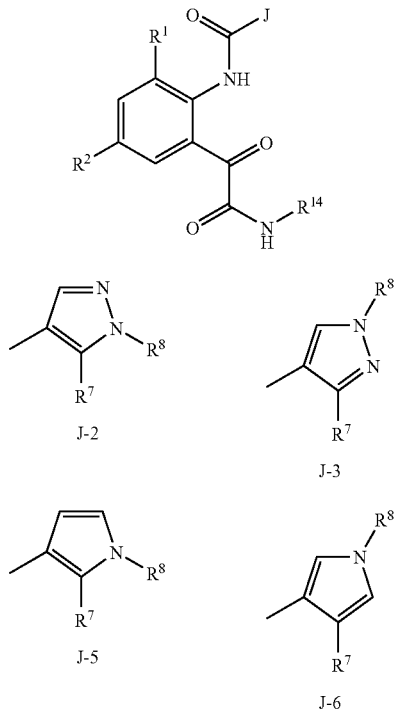

| J | R¹ | R² | R⁷ | R⁸ | R¹⁴ |
|---|---|---|---|---|---|
| J-2 | Me | Cl | 2-Cl-Ph | CH$_2$CF$_3$ | Me |
| J-2 | Me | Cl | 2-Cl-Ph | CHF$_2$ | Me |
| J-2 | Me | Cl | 3-Cl-2-Py | CH$_2$CF$_3$ | Me |
| J-2 | Me | Cl | 3-Cl-2-Py | CHF$_2$ | Me |
| J-2 | Me | CN | 2-Cl-Ph | CH$_2$CF$_3$ | Me |
| J-2 | Me | CN | 2-Cl-Ph | CHF$_2$ | Me |
| J-2 | Me | CN | 3-Cl-2-Py | CH$_2$CF$_3$ | Me |
| J-2 | Me | CN | 3-Cl-2-Py | CHF$_2$ | Me |
| J-2 | Cl | Cl | 2-Cl-Ph | CH$_2$CF$_3$ | Me |
| J-2 | Cl | Cl | 2-Cl-Ph | CHF$_2$ | Me |
| J-2 | Cl | Cl | 3-Cl-2-Py | CH$_2$CF$_3$ | Me |
| J-2 | Cl | Cl | 3-Cl-2-Py | CHF$_2$ | Me |
| J-2 | Br | Br | 2-Cl-Ph | CH$_2$CF$_3$ | Me |
| J-2 | Br | Br | 2-Cl-Ph | CHF$_2$ | Me |
| J-2 | Br | Br | 3-Cl-2-Py | CH$_2$CF$_3$ | Me |
| J-2 | Br | Br | 3-Cl-2-Py | CHF$_2$ | Me |
| J-3 | Me | Cl | 2-Cl-Ph | CH$_2$CF$_3$ | Me |
| J-3 | Me | Cl | 2-Cl-Ph | CHF$_2$ | Me |
| J-3 | Me | Cl | 3-Cl-2-Py | CH$_2$CF$_3$ | Me |
| J-3 | Me | Cl | 3-Cl-2-Py | CHF$_2$ | Me |
| J-3 | Me | CN | 2-Cl-Ph | CH$_2$CF$_3$ | Me |
| J-3 | Me | CN | 2-Cl-Ph | CHF$_2$ | Me |
| J-3 | Me | CN | 3-Cl-2-Py | CH$_2$CF$_3$ | Me |
| J-3 | Me | CN | 3-Cl-2-Py | CHF$_2$ | Me |
| J-3 | Cl | Cl | 2-Cl-Ph | CH$_2$CF$_3$ | Me |
| J-3 | Cl | Cl | 2-Cl-Ph | CHF$_2$ | Me |
| J-3 | Cl | Cl | 3-Cl-2-Py | CH$_2$CF$_3$ | Me |
| J-3 | Cl | Cl | 3-Cl-2-Py | CHF$_2$ | Me |
| J-3 | Br | Br | 2-Cl-Ph | CH$_2$CF$_3$ | Me |
| J-3 | Br | Br | 2-Cl-Ph | CHF$_2$ | Me |
| J-3 | Br | Br | 3-Cl-2-Py | CH$_2$CF$_3$ | Me |
| J-3 | Br | Br | 3-Cl-2-Py | CHF$_2$ | Me |
| J-5 | Me | Cl | 2-Cl-Ph | CH$_2$CF$_3$ | Me |
| J-5 | Me | Cl | 2-Cl-Ph | CHF$_2$ | Me |
| J-5 | Me | Cl | 3-Cl-2-Py | CH$_2$CF$_3$ | Me |
| J-5 | Me | Cl | 3-Cl-2-Py | CHF$_2$ | Me |
| J-5 | Me | CN | 2-Cl-Ph | CH$_2$CF$_3$ | Me |
| J-5 | Me | CN | 2-Cl-Ph | CHF$_2$ | Me |
| J-5 | Me | CN | 3-Cl-2-Py | CH$_2$CF$_3$ | Me |
| J-5 | Me | CN | 3-Cl-2-Py | CHF$_2$ | Me |
| J-5 | Cl | Cl | 2-Cl-Ph | CH$_2$CF$_3$ | Me |
| J-5 | Cl | Cl | 2-Cl-Ph | CHF$_2$ | Me |
| J-5 | Cl | Cl | 3-Cl-2-Py | CH$_2$CF$_3$ | Me |
| J-5 | Cl | Cl | 3-Cl-2-Py | CHF$_2$ | Me |
| J-5 | Br | Br | 2-Cl-Ph | CH$_2$CF$_3$ | Me |
| J-5 | Br | Br | 2-Cl-Ph | CHF$_2$ | Me |
| J-5 | Br | Br | 3-Cl-2-Py | CH$_2$CF$_3$ | Me |
| J-5 | Br | Br | 3-Cl-2-Py | CHF$_2$ | Me |
| J-6 | Me | Cl | 2-Cl-Ph | CH$_2$CF$_3$ | Me |
| J-6 | Me | Cl | 2-Cl-Ph | CHF$_2$ | Me |
| J-6 | Me | Cl | 3-Cl-2-Py | CH$_2$CF$_3$ | Me |
| J-6 | Me | Cl | 3-Cl-2-Py | CHF$_2$ | Me |
| J-6 | Me | CN | 2-Cl-Ph | CH$_2$CF$_3$ | Me |
| J-6 | Me | CN | 2-Cl-Ph | CHF$_2$ | Me |
| J-6 | Me | CN | 3-Cl-2-Py | CH$_2$CF$_3$ | Me |
| J-6 | Me | CN | 3-Cl-2-Py | CHF$_2$ | Me |
| J-6 | Cl | Cl | 2-Cl-Ph | CH$_2$CF$_3$ | Me |
| J-6 | Cl | Cl | 2-Cl-Ph | CHF$_2$ | Me |
| J-6 | Cl | Cl | 3-Cl-2-Py | CH$_2$CF$_3$ | Me |
| J-6 | Cl | Cl | 3-Cl-2-Py | CHF$_2$ | Me |
| J-6 | Br | Br | 2-Cl-Ph | CH$_2$CF$_3$ | Me |
| J-6 | Br | Br | 2-Cl-Ph | CHF$_2$ | Me |
| J-6 | Br | Br | 3-Cl-2-Py | CH$_2$CF$_3$ | Me |
| J-6 | Br | Br | 3-Cl-2-Py | CHF$_2$ | Me |
| J-2 | Me | Cl | 2-Cl-Ph | CH$_2$CF$_3$ | i-Pr |
| J-2 | Me | Cl | 2-Cl-Ph | CHF$_2$ | i-Pr |
| J-2 | Me | Cl | 3-Cl-2-Py | CH$_2$CF$_3$ | i-Pr |
| J-2 | Me | Cl | 3-Cl-2-Py | CHF$_2$ | i-Pr |
| J-2 | Me | CN | 2-Cl-Ph | CH$_2$CF$_3$ | i-Pr |
| J-2 | Me | CN | 2-Cl-Ph | CHF$_2$ | i-Pr |
| J-2 | Me | CN | 3-Cl-2-Py | CH$_2$CF$_3$ | i-Pr |
| J-2 | Me | CN | 3-Cl-2-Py | CHF$_2$ | i-Pr |
| J-2 | Cl | Cl | 2-Cl-Ph | CH$_2$CF$_3$ | i-Pr |
| J-2 | Cl | Cl | 2-Cl-Ph | CHF$_2$ | i-Pr |
| J-2 | Cl | Cl | 3-Cl-2-Py | CH$_2$CF$_3$ | i-Pr |
| J-2 | Cl | Cl | 3-Cl-2-Py | CHF$_2$ | i-Pr |
| J-2 | Br | Br | 2-Cl-Ph | CH$_2$CF$_3$ | i-Pr |
| J-2 | Br | Br | 2-Cl-Ph | CHF$_2$ | i-Pr |
| J-2 | Br | Br | 3-Cl-2-Py | CH$_2$CF$_3$ | i-Pr |
| J-2 | Br | Br | 3-Cl-2-Py | CHF$_2$ | i-Pr |
| J-3 | Me | Cl | 2-Cl-Ph | CH$_2$CF$_3$ | i-Pr |
| J-3 | Me | Cl | 2-Cl-Ph | CHF$_2$ | i-Pr |
| J-3 | Me | Cl | 3-Cl-2-Py | CH$_2$CF$_3$ | i-Pr |
| J-3 | Me | Cl | 3-Cl-2-Py | CHF$_2$ | i-Pr |
| J-3 | Me | CN | 2-Cl-Ph | CH$_2$CF$_3$ | i-Pr |
| J-3 | Me | CN | 2-Cl-Ph | CHF$_2$ | i-Pr |
| J-3 | Me | CN | 3-Cl-2-Py | CH$_2$CF$_3$ | i-Pr |
| J-3 | Me | CN | 3-Cl-2-Py | CHF$_2$ | i-Pr |
| J-3 | Cl | Cl | 2-Cl-Ph | CH$_2$CF$_3$ | i-Pr |
| J-3 | Cl | Cl | 2-Cl-Ph | CHF$_2$ | i-Pr |
| J-3 | Cl | Cl | 3-Cl-2-Py | CH$_2$CF$_3$ | i-Pr |
| J-3 | Cl | Cl | 3-Cl-2-Py | CHF$_2$ | i-Pr |
| J-3 | Br | Br | 2-Cl-Ph | CH$_2$CF$_3$ | i-Pr |
| J-3 | Br | Br | 2-Cl-Ph | CHF$_2$ | i-Pr |
| J-3 | Br | Br | 3-Cl-2-Py | CH$_2$CF$_3$ | i-Pr |
| J-3 | Br | Br | 3-Cl-2-Py | CHF$_2$ | i-Pr |
| J-5 | Me | Cl | 2-Cl-Ph | CH$_2$CF$_3$ | i-Pr |
| J-5 | Me | Cl | 2-Cl-Ph | CHF$_2$ | i-Pr |
| J-5 | Me | Cl | 3-Cl-2-Py | CH$_2$CF$_3$ | i-Pr |
| J-5 | Me | Cl | 3-Cl-2-Py | CHF$_2$ | i-Pr |
| J-5 | Me | CN | 2-Cl-Ph | CH$_2$CF$_3$ | i-Pr |
| J-5 | Me | CN | 2-Cl-Ph | CHF$_2$ | i-Pr |
| J-5 | Me | CN | 3-Cl-2-Py | CH$_2$CF$_3$ | i-Pr |
| J-5 | Me | CN | 3-Cl-2-Py | CHF$_2$ | i-Pr |
| J-5 | Cl | Cl | 2-Cl-Ph | CH$_2$CF$_3$ | i-Pr |
| J-5 | Cl | Cl | 2-Cl-Ph | CHF$_2$ | i-Pr |
| J-5 | Cl | Cl | 3-Cl-2-Py | CH$_2$CF$_3$ | i-Pr |
| J-5 | Cl | Cl | 3-Cl-2-Py | CHF$_2$ | i-Pr |
| J-5 | Br | Br | 2-Cl-Ph | CH$_2$CF$_3$ | i-Pr |
| J-5 | Br | Br | 2-Cl-Ph | CHF$_2$ | i-Pr |
| J-5 | Br | Br | 3-Cl-2-Py | CH$_2$CF$_3$ | i-Pr |
| J-5 | Br | Br | 3-Cl-2-Py | CHF$_2$ | i-Pr |
| J-6 | Me | Cl | 2-Cl-Ph | CH$_2$CF$_3$ | i-Pr |
| J-6 | Me | Cl | 2-Cl-Ph | CHF$_2$ | i-Pr |
| J-6 | Me | Cl | 3-Cl-2-Py | CH$_2$CF$_3$ | i-Pr |
| J-6 | Me | Cl | 3-Cl-2-Py | CHF$_2$ | i-Pr |
| J-6 | Me | CN | 2-Cl-Ph | CH$_2$CF$_3$ | i-Pr |
| J-6 | Me | CN | 2-Cl-Ph | CHF$_2$ | i-Pr |
| J-6 | Me | CN | 3-Cl-2-Py | CH$_2$CF$_3$ | i-Pr |
| J-6 | Me | CN | 3-Cl-2-Py | CHF$_2$ | i-Pr |
| J-6 | Cl | Cl | 2-Cl-Ph | CH$_2$CF$_3$ | i-Pr |

TABLE 2-continued

| J | | | | | |
|---|---|---|---|---|---|
| J-6 | Cl | Cl | 2-Cl-Ph | CHF$_2$ | i-Pr |
| J-6 | Cl | Cl | 3-Cl-2-Py | CH$_2$CF$_3$ | i-Pr |
| J-6 | Cl | Cl | 3-Cl-2-Py | CHF$_2$ | i-Pr |
| J-6 | Br | Br | 2-Cl-Ph | CH$_2$CF$_3$ | i-Pr |
| J-6 | Br | Br | 2-Cl-Ph | CHF$_2$ | i-Pr |
| J-6 | Br | Br | 3-Cl-2-Py | CH$_2$CF$_3$ | i-Pr |
| J-6 | Br | Br | 3-Cl-2-Py | CHF$_2$ | i-Pr |

TABLE 3

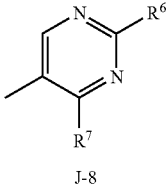

| J | R$^1$ | R$^2$ | R$^7$ | R$^6$ | R$^{14}$ |
|---|---|---|---|---|---|
| J-4 | Me | Cl | 2-Cl-Ph | 4-Br | Me |
| J-4 | Me | Cl | 2-Cl-Ph | 5-Br | Me |
| J-4 | Me | Cl | 3-Cl-2-Py | 4-Br | Me |
| J-4 | Me | Cl | 3-Cl-2-Py | 5-Br | Me |
| J-4 | Me | CN | 2-Cl-Ph | 4-Br | Me |
| J-4 | Me | CN | 2-Cl-Ph | 5-Br | Me |
| J-4 | Me | CN | 3-Cl-2-Py | 4-Br | Me |
| J-4 | Me | CN | 3-Cl-2-Py | 5-Br | Me |
| J-4 | Cl | Cl | 2-Cl-Ph | 4-Br | Me |
| J-4 | Cl | Cl | 2-Cl-Ph | 5-Br | Me |
| J-4 | Cl | Cl | 3-Cl-2-Py | 4-Br | Me |
| J-4 | Cl | Cl | 3-Cl-2-Py | 5-Br | Me |
| J-4 | Br | Br | 2-Cl-Ph | 4-Br | Me |
| J-4 | Br | Br | 2-Cl-Ph | 5-Br | Me |
| J-4 | Br | Br | 3-Cl-2-Py | 4-Br | Me |
| J-4 | Br | Br | 3-Cl-2-Py | 5-Br | Me |
| J-7 | Me | Cl | 2-Cl-Ph | CF$_3$ | Me |
| J-7 | Me | Cl | 3-Cl-2-Py | CF$_3$ | Me |
| J-7 | Me | CN | 2-Cl-Ph | CF$_3$ | Me |
| J-7 | Me | CN | 3-Cl-2-Py | CF$_3$ | Me |
| J-7 | Cl | Cl | 2-Cl-Ph | CF$_3$ | Me |
| J-7 | Cl | Cl | 3-Cl-2-Py | CF$_3$ | Me |
| J-7 | Br | Br | 2-Cl-Ph | CF$_3$ | Me |
| J-7 | Br | Br | 3-Cl-2-Py | CF$_3$ | Me |
| J-8 | Me | Cl | 2-Cl-Ph | CF$_3$ | Me |
| J-8 | Me | Cl | 3-Cl-2-Py | CF$_3$ | Me |
| J-8 | Me | CN | 2-Cl-Ph | CF$_3$ | Me |
| J-8 | Me | CN | 3-Cl-2-Py | CF$_3$ | Me |
| J-8 | Cl | Cl | 2-Cl-Ph | CF$_3$ | Me |
| J-8 | Cl | Cl | 3-Cl-2-Py | CF$_3$ | Me |
| J-8 | Br | Br | 2-Cl-Ph | CF$_3$ | Me |
| J-8 | Br | Br | 3-Cl-2-Py | CF$_3$ | Me |
| J-4 | Me | Cl | 2-Cl-Ph | 4-Br | i-Pr |
| J-4 | Me | Cl | 2-Cl-Ph | 5-Br | i-Pr |
| J-4 | Me | Cl | 3-Cl-2-Py | 4-Br | i-Pr |
| J-4 | Me | Cl | 3-Cl-2-Py | 5-Br | i-Pr |
| J-4 | Me | CN | 2-Cl-Ph | 4-Br | i-Pr |
| J-4 | Me | CN | 2-Cl-Ph | 5-Br | i-Pr |
| J-4 | Me | CN | 3-Cl-2-Py | 4-Br | i-Pr |
| J-4 | Me | CN | 3-Cl-2-Py | 5-Br | i-Pr |
| J-4 | Cl | Cl | 2-Cl-Ph | 4-Br | i-Pr |

TABLE 3-continued

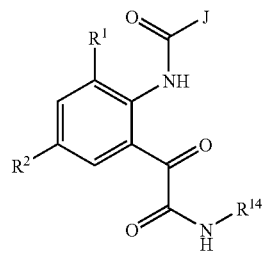

| J | R$^1$ | R$^2$ | R$^7$ | R$^6$ | R$^{14}$ |
|---|---|---|---|---|---|
| J-4 | Cl | Cl | 2-Cl-Ph | 5-Br | i-Pr |
| J-4 | Cl | Cl | 3-Cl-2-Py | 4-Br | i-Pr |
| J-4 | Cl | Cl | 3-Cl-2-Py | 5-Br | i-Pr |
| J-4 | Br | Br | 2-Cl-Ph | 4-Br | i-Pr |
| J-4 | Br | Br | 2-Cl-Ph | 5-Br | i-Pr |
| J-4 | Br | Br | 3-Cl-2-Py | 4-Br | i-Pr |
| J-4 | Br | Br | 3-Cl-2-Py | 5-Br | i-Pr |
| J-7 | Me | Cl | 2-Cl-Ph | CF3 | i-Pr |
| J-7 | Me | Cl | 3-Cl-2-Py | CF$_3$ | i-Pr |
| J-7 | Me | CN | 2-Cl-Ph | CF$_3$ | i-Pr |
| J-7 | Me | CN | 3-Cl-2-Py | CF$_3$ | i-Pr |
| J-7 | Cl | Cl | 2-Cl-Ph | CF$_3$ | i-Pr |
| J-7 | Cl | Cl | 3-Cl-2-Py | CF$_3$ | i-Pr |
| J-7 | Br | Br | 2-Cl-Ph | CF$_3$ | i-Pr |
| J-7 | Br | Br | 3-Cl-2-Py | CF$_3$ | i-Pr |
| J-8 | Me | Cl | 2-Cl-Ph | CF$_3$ | i-Pr |
| J-8 | Me | Cl | 3-Cl-2-Py | CF$_3$ | i-Pr |
| J-8 | Me | CN | 2-Cl-Ph | CF$_3$ | i-Pr |
| J-8 | Me | CN | 3-Cl-2-Py | CF$_3$ | i-Pr |
| J-8 | Cl | Cl | 2-Cl-Ph | CF$_3$ | i-Pr |
| J-8 | Cl | Cl | 3-Cl-2-Py | CF$_3$ | i-Pr |
| J-8 | Br | Br | 2-Cl-Ph | CF$_3$ | i-Pr |
| J-8 | Br | Br | 3-Cl-2-Py | CF$_3$ | i-Pr |

TABLE 4

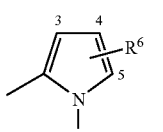

| R$^1$ | R$^2$ | R$^6$ | X | R$^{11}$ | R$^{12}$ | R$^{14}$ | R$^{15}$ |
|---|---|---|---|---|---|---|---|
| Me | Cl | CF$_3$ | CH | H | H | Me | H |
| Me | Cl | Br | CH | H | H | Me | H |
| Me | Cl | Cl | CH | H | H | Me | H |
| Me | Br | CF$_3$ | CH | H | H | Me | H |
| Me | Br | Br | CH | H | H | Me | H |

TABLE 4-continued

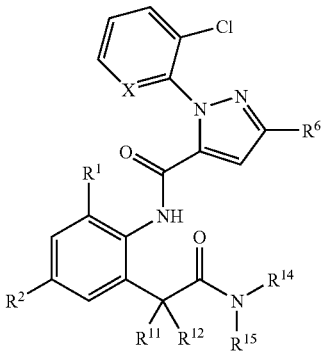

| R¹ | R² | R⁶ | X | R¹¹ | R¹² | R¹⁴ | R¹⁵ |
|---|---|---|---|---|---|---|---|
| Me | Br | Cl | CH | H | H | Me | H |
| Me | CN | CF₃ | CH | H | H | Me | H |
| Me | CN | Br | CH | H | H | Me | H |
| Me | CN | Cl | CH | H | H | Me | H |
| Cl | Cl | CF₃ | CH | H | H | Me | H |
| Cl | Cl | Br | CH | H | H | Me | H |
| Cl | Cl | Cl | CH | H | H | Me | H |
| Br | Br | CF₃ | CH | H | H | Me | H |
| Br | Br | Br | CH | H | H | Me | H |
| Br | Br | Cl | CH | H | H | Me | H |
| Me | Cl | CF₃ | N | H | H | Me | H |
| Me | Cl | Br | N | H | H | Me | H |
| Me | Cl | Cl | N | H | H | Me | H |
| Me | Br | CF₃ | N | H | H | Me | H |
| Me | Br | Br | N | H | H | Me | H |
| Me | Br | Cl | N | H | H | Me | H |
| Me | CN | CF₃ | N | H | H | Me | H |
| Me | CN | Br | N | H | H | Me | H |
| Me | CN | Cl | N | H | H | Me | H |
| Cl | Cl | CF₃ | N | H | H | Me | H |
| Cl | Cl | Br | N | H | H | Me | H |
| Cl | Cl | Cl | N | H | H | Me | H |
| Br | Br | CF₃ | N | H | H | Me | H |
| Br | Br | Br | N | H | H | Me | H |
| Br | Br | Cl | N | H | H | Me | H |
| Me | Cl | CF₃ | CH | H | H | Et | H |
| Me | Cl | Br | CH | H | H | Et | H |
| Me | Cl | Cl | CH | H | H | Et | H |
| Me | Br | CF₃ | CH | H | H | Et | H |
| Me | Br | Br | CH | H | H | Et | H |
| Me | Br | Cl | CH | H | H | Et | H |
| Me | CN | CF₃ | CH | H | H | Et | H |
| Me | CN | Br | CH | H | H | Et | H |
| Me | CN | Cl | CH | H | H | Et | H |
| Cl | Cl | CF₃ | CH | H | H | Et | H |
| Cl | Cl | Br | CH | H | H | Et | H |
| Cl | Cl | Cl | CH | H | H | Et | H |
| Br | Br | CF₃ | CH | H | H | Et | H |
| Br | Br | Br | CH | H | H | Et | H |
| Br | Br | Cl | CH | H | H | Et | H |
| Me | Cl | CF₃ | N | H | H | Et | H |
| Me | Cl | Br | N | H | H | Et | H |
| Me | Cl | Cl | N | H | H | Et | H |
| Me | Br | CF₃ | N | H | H | Et | H |
| Me | Br | Br | N | H | H | Et | H |
| Me | Br | Cl | N | H | H | Et | H |
| Me | CN | CF₃ | N | H | H | Et | H |
| Me | CN | Br | N | H | H | Et | H |
| Me | CN | Cl | N | H | H | Et | H |
| Cl | Cl | CF₃ | N | H | H | Et | H |
| Cl | Cl | Br | N | H | H | Et | H |
| Cl | Cl | Cl | N | H | H | Et | H |
| Br | Br | CF₃ | N | H | H | Et | H |
| Br | Br | Br | N | H | H | Et | H |
| Br | Br | Cl | N | H | H | Et | H |
| Me | Cl | CF₃ | CH | H | H | i-Pr | H |
| Me | Cl | Br | CH | H | H | i-Pr | H |
| Me | Cl | Cl | CH | H | H | i-Pr | H |
| Me | Br | CF₃ | CH | H | H | i-Pr | H |

TABLE 4-continued

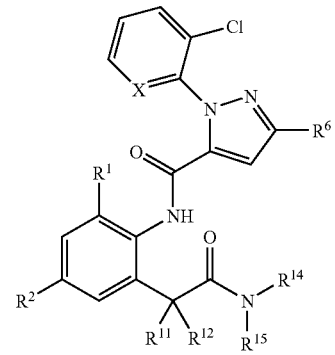

| R¹ | R² | R⁶ | X | R¹¹ | R¹² | R¹⁴ | R¹⁵ |
|---|---|---|---|---|---|---|---|
| Me | Br | Br | CH | H | H | i-Pr | H |
| Me | Br | Cl | CH | H | H | i-Pr | H |
| Me | CN | CF₃ | CH | H | H | i-Pr | H |
| Me | CN | Br | CH | H | H | i-Pr | H |
| Me | CN | Cl | CH | H | H | i-Pr | H |
| Cl | Cl | CF₃ | CH | H | H | i-Pr | H |
| Cl | Cl | Br | CH | H | H | i-Pr | H |
| Cl | Cl | Cl | CH | H | H | i-Pr | H |
| Br | Br | CF₃ | CH | H | H | i-Pr | H |
| Br | Br | Br | CH | H | H | i-Pr | H |
| Br | Br | Cl | CH | H | H | i-Pr | H |
| Me | Cl | CF₃ | N | H | H | i-Pr | H |
| Me | Cl | Br | N | H | H | i-Pr | H |
| Me | Cl | Cl | N | H | H | i-Pr | H |
| Me | Br | CF₃ | N | H | H | i-Pr | H |
| Me | Br | Br | N | H | H | i-Pr | H |
| Me | Br | Cl | N | H | H | i-Pr | H |
| Me | CN | CF₃ | N | H | H | i-Pr | H |
| Me | CN | Br | N | H | H | i-Pr | H |
| Me | CN | Cl | N | H | H | i-Pr | H |
| Cl | Cl | CF₃ | N | H | H | i-Pr | H |
| Cl | Cl | Br | N | H | H | i-Pr | H |
| Cl | Cl | Cl | N | H | H | i-Pr | H |
| Br | Br | CF₃ | N | H | H | i-Pr | H |
| Br | Br | Br | N | H | H | i-Pr | H |
| Br | Br | Cl | N | H | H | i-Pr | H |
| Me | Cl | CF₃ | CH | H | H | t-Bu | H |
| Me | Cl | Br | CH | H | H | t-Bu | H |
| Me | Cl | Cl | CH | H | H | t-Bu | H |
| Me | Br | CF₃ | CH | H | H | t-Bu | H |
| Me | Br | Br | CH | H | H | t-Bu | H |
| Me | Br | Cl | CH | H | H | t-Bu | H |
| Me | CN | CF₃ | CH | H | H | t-Bu | H |
| Me | CN | Br | CH | H | H | t-Bu | H |
| Me | CN | Cl | CH | H | H | t-Bu | H |
| Cl | Cl | CF₃ | CH | H | H | t-Bu | H |
| Cl | Cl | Br | CH | H | H | t-Bu | H |
| Cl | Cl | Cl | CH | H | H | t-Bu | H |
| Br | Br | CF₃ | CH | H | H | t-Bu | H |
| Br | Br | Br | CH | H | H | t-Bu | H |
| Br | Br | Cl | CH | H | H | t-Bu | H |
| Me | Cl | CF₃ | N | H | H | t-Bu | H |
| Me | Cl | Br | N | H | H | t-Bu | H |
| Me | Cl | Cl | N | H | H | t-Bu | H |
| Me | Br | CF₃ | N | H | H | t-Bu | H |
| Me | Br | Br | N | H | H | t-Bu | H |
| Me | Br | Cl | N | H | H | t-Bu | H |
| Me | CN | CF₃ | N | H | H | t-Bu | H |
| Me | CN | Br | N | H | H | t-Bu | H |
| Me | CN | Cl | N | H | H | t-Bu | H |
| Cl | Cl | CF₃ | N | H | H | t-Bu | H |
| Cl | Cl | Br | N | H | H | t-Bu | H |
| Cl | Cl | Cl | N | H | H | t-Bu | H |
| Br | Br | CF₃ | N | H | H | t-Bu | H |
| Br | Br | Br | N | H | H | t-Bu | H |
| Br | Br | Cl | N | H | H | t-Bu | H |
| Me | Cl | CF₃ | CH | H | H | Me | Me |
| Me | Cl | Br | CH | H | H | Me | Me |
| Me | Cl | Cl | CH | H | H | Me | Me |

TABLE 4-continued

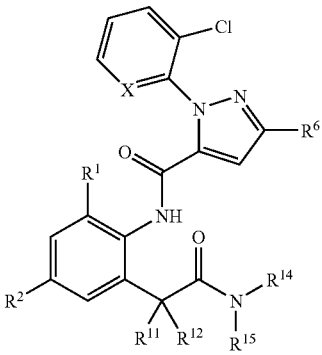

| R¹ | R² | R⁶ | X | R¹¹ | R¹² | R¹⁴ | R¹⁵ |
|---|---|---|---|---|---|---|---|
| Me | Br | CF₃ | CH | H | H | Me | Me |
| Me | Br | Br | CH | H | H | Me | Me |
| Me | Br | Cl | CH | H | H | Me | Me |
| Me | CN | CF₃ | CH | H | H | Me | Me |
| Me | CN | Br | CH | H | H | Me | Me |
| Me | CN | Cl | CH | H | H | Me | Me |
| Cl | Cl | CF₃ | CH | H | H | Me | Me |
| Cl | Cl | Br | CH | H | H | Me | Me |
| Cl | Cl | Cl | CH | H | H | Me | Me |
| Br | Br | CF₃ | CH | H | H | Me | Me |
| Br | Br | Br | CH | H | H | Me | Me |
| Br | Br | Cl | CH | H | H | Me | Me |
| Me | Cl | CF₃ | N | H | H | Me | Me |
| Me | Cl | Br | N | H | H | Me | Me |
| Me | Cl | Cl | N | H | H | Me | Me |
| Me | Br | CF₃ | N | H | H | Me | Me |
| Me | Br | Br | N | H | H | Me | Me |
| Me | Br | Cl | N | H | H | Me | Me |
| Me | CN | CF₃ | N | H | H | Me | Me |
| Me | CN | Br | N | H | H | Me | Me |
| Me | CN | Cl | N | H | H | Me | Me |
| Cl | Cl | CF₃ | N | H | H | Me | Me |
| Cl | Cl | Br | N | H | H | Me | Me |
| Cl | Cl | Cl | N | H | H | Me | Me |
| Br | Br | CF₃ | N | H | H | Me | Me |
| Br | Br | Br | N | H | H | Me | Me |
| Br | Br | Cl | N | H | H | Me | Me |
| Me | Cl | CF₃ | N | OH | H | Me | H |
| Me | Cl | Br | N | OH | H | Me | H |
| Me | Cl | Cl | N | OH | H | Me | H |
| Me | Br | CF₃ | N | OH | H | Me | H |
| Me | Br | Br | N | OH | H | Me | H |
| Me | Br | Cl | N | OH | H | Me | H |
| Me | CN | CF₃ | N | OH | H | Me | H |
| Me | CN | Br | N | OH | H | Me | H |
| Me | CN | Cl | N | OH | H | Me | H |
| Me | Cl | CF₃ | N | OMe | H | Me | H |
| Me | Cl | Br | N | OMe | H | Me | H |
| Me | Cl | Cl | N | OMe | H | Me | H |
| Me | Br | CF₃ | N | OMe | H | Me | H |
| Me | Br | Br | N | OMe | H | Me | H |
| Me | Br | Cl | N | OMe | H | Me | H |
| Me | CN | CF₃ | N | OMe | H | Me | H |
| Me | CN | Br | N | OMe | H | Me | H |
| Me | CN | Cl | N | OMe | H | Me | H |
| Me | Cl | CF₃ | N | Me | H | Me | H |
| Me | Cl | Br | N | Me | H | Me | H |
| Me | Cl | Cl | N | Me | H | Me | H |
| Me | Br | CF₃ | N | Me | H | Me | H |
| Me | Br | Br | N | Me | H | Me | H |
| Me | Br | Cl | N | Me | H | Me | H |
| Me | CN | CF₃ | N | Me | H | Me | H |
| Me | CN | Br | N | Me | H | Me | H |
| Me | CN | Cl | N | Me | H | Me | H |
| Me | Cl | CF₃ | N | Me | Me | Me | H |
| Me | Cl | Br | N | Me | Me | Me | H |
| Me | Cl | Cl | N | Me | Me | Me | H |
| Me | Br | CF₃ | N | Me | Me | Me | H |
| Me | Br | Br | N | Me | Me | Me | H |

TABLE 4-continued

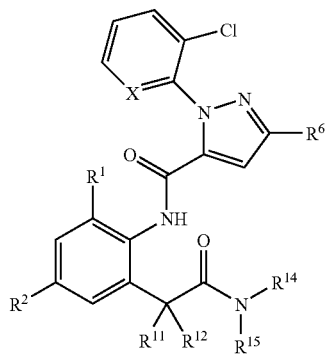

| R¹ | R² | R⁶ | X | R¹¹ | R¹² | R¹⁴ | R¹⁵ |
|---|---|---|---|---|---|---|---|
| Me | Br | Cl | N | Me | Me | Me | H |
| Me | CN | CF₃ | N | Me | Me | Me | H |
| Me | CN | Br | N | Me | Me | Me | H |
| Me | CN | Cl | N | Me | Me | Me | H |

TABLE 5

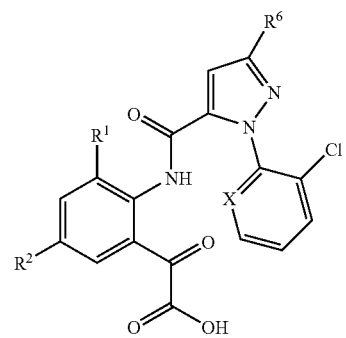

| R¹ | R² | R⁶ | X |
|---|---|---|---|
| Me | Cl | CF₃ | CH |
| Me | Cl | Br | CH |
| Me | Cl | Cl | CH |
| Me | Br | CF₃ | CH |
| Me | Br | Br | CH |
| Me | Br | Cl | CH |
| Me | CN | CF₃ | CH |
| Me | CN | Br | CH |
| Me | CN | Cl | CH |
| Cl | Cl | CF₃ | CH |
| Cl | Cl | Br | CH |
| Cl | Cl | Cl | CH |
| Br | Br | CF₃ | CH |
| Br | Br | Br | CH |
| Br | Br | Cl | CH |
| Me | Cl | CF₃ | N |
| Me | Cl | Br | N |
| Me | Cl | Cl | N |
| Me | Br | CF₃ | N |
| Me | Br | Br | N |
| Me | Br | Cl | N |
| Me | CN | CF₃ | N |
| Me | CN | Br | N |
| Me | CN | Cl | N |
| Cl | Cl | CF₃ | N |
| Cl | Cl | Br | N |
| Cl | Cl | Cl | N |

TABLE 5-continued

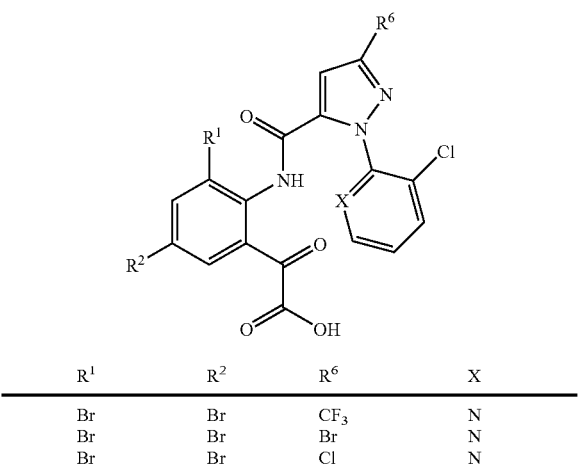

| R¹ | R² | R⁶ | X |
|---|---|---|---|
| Br | Br | CF₃ | N |
| Br | Br | Br | N |
| Br | Br | Cl | N |

TABLE 6

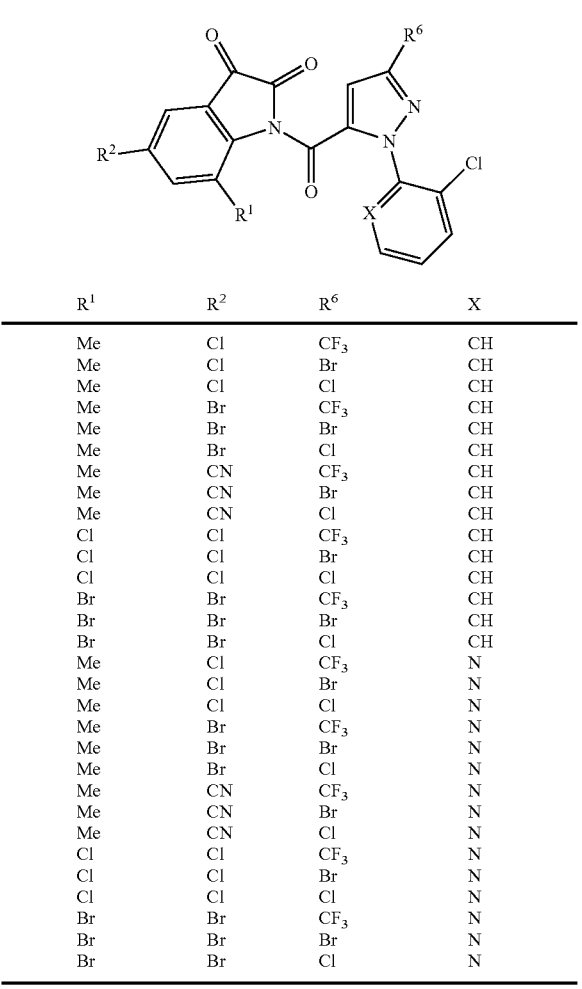

| R¹ | R² | R⁶ | X |
|---|---|---|---|
| Me | Cl | CF₃ | CH |
| Me | Cl | Br | CH |
| Me | Cl | Cl | CH |
| Me | Br | CF₃ | CH |
| Me | Br | Br | CH |
| Me | Br | Cl | CH |
| Me | CN | CF₃ | CH |
| Me | CN | Br | CH |
| Me | CN | Cl | CH |
| Cl | Cl | CF₃ | CH |
| Cl | Cl | Br | CH |
| Cl | Cl | Cl | CH |
| Br | Br | CF₃ | CH |
| Br | Br | Br | CH |
| Br | Br | Cl | CH |
| Me | Cl | CF₃ | N |
| Me | Cl | Br | N |
| Me | Cl | Cl | N |
| Me | Br | CF₃ | N |
| Me | Br | Br | N |
| Me | Br | Cl | N |
| Me | CN | CF₃ | N |
| Me | CN | Br | N |
| Me | CN | Cl | N |
| Cl | Cl | CF₃ | N |
| Cl | Cl | Br | N |
| Cl | Cl | Cl | N |
| Br | Br | CF₃ | N |
| Br | Br | Br | N |
| Br | Br | Cl | N |

Formulation/Utility

Compounds of this invention will generally be used as a formulation or composition with a suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films (including seed coatings), and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 0.001-90 | 0-99.999 | 0-15 |
| Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, glycerol esters, polyoxyethylene/polyoxypropylene block copolymers, and alkylpolyglycosides where the number of glucose units, referred to as degree of polymerization (D.P.), can range from 1 to 3 and the alkyl units can range from $C_6$ to $C_{14}$ (see *Pure and Applied Chemistry* 72, 1255-1264). Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, propylene carbonate, dibasic esters, paraffins, alkylbenzenes, alkylnaphthalenes, glycerine, triacetine, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, acetates such as hexyl acetate, heptyl acetate and octyl acetate, and alcohols such as methanol, cyclohexanol, decanol, benzyl and tetrahydrofurfuryl alcohol.

Useful formulations of this invention may also contain materials well known to those skilled in the art as formulation aids such as antifoams, film formers and dyes. Antifoams can include water dispersible liquids comprising polyorganosiloxanes like Rhodorsil® 416. The film formers can include polyvinyl acetates, polyvinyl acetate copolymers, polyvinylpyrrolidone-vinyl acetate copolymer, polyvinyl alcohols, polyvinyl alcohol copolymers and waxes. Dyes can include water dispersible liquid colorant compositions like Pro-lzed® Colorant Red. One skilled in the art will appreciate that this is a non-exhaustive list of formulation aids. Suitable examples of formulation aids include those listed herein and those listed in *McCutcheon's 2001, Volume 2: Functional Materials* published by MC Publishing Company and PCT Publication WO 03/024222.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-E. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

EXAMPLE A

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE B

| Granule | |
|---|---|
| Compound 11 | 10.0% |
| attapulgite granules (low volatile matter, 0.71/0.30 mm; U.S.S. No. 25-50 sieves) | 90.0% |

EXAMPLE C

| Extruded Pellet | |
|---|---|
| Compound 3 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE D

| Emulsifiable Concentrate | |
|---|---|
| Compound 8 | 20.0% |
| blend of oil soluble sulfonates and polyoxyethylene ethers | 10.0% |
| isophorone | 70.0% |

EXAMPLE E

| Microemulsion | |
|---|---|
| Compound 12 | 5.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE F

| Seed Treatment | |
|---|---|
| Compound 14 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

EXAMPLE G

| Fertilizer Stick | |
|---|---|
| Compound 1 | 2.50% |
| pyrrolidone-styrene copolymer | 4.80% |
| tristyrylphenyl 16-ethoxylate | 2.30% |
| talc | 0.80% |
| corn starch | 5.00% |
| Nitrophoska ® Permanent 15-9-15 slow-release fertilizer (BASF) | 36.00% |
| kaolin | 38.00% |
| water | 10.60% |

Compounds of this invention are characterized by favorable metabolic and/or soil residual patterns and exhibit activity controlling a spectrum of agronomic and nonagronomic invertebrate pests. Compounds of this invention are also characterized by favorable foliar and or soil-applied systemicity in plants exhibiting translocation to protect foliage and other plant parts not directly contacted with invertebrate pest control compositions comprising the present compounds. In the context of this disclosure "invertebrate pest control" means inhibition of invertebrate pest development (including mortality, feeding reduction, and/or mating disruption) and as a result significant reduction in feeding or injury to an agronomic crop or damage to a building structure caused by the invertebrate pest; related expressions are defined analogously.

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives). The term "agronomic" also refers to the production of such crops that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high and low temperatures, low or high soil moisture, and high salinity, increased flowering or fruiting, greater harvest yields, more rapid maturation, higher quality and/or nutritional value of the harvested product, and improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringienlsis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetylactate synthase (ALS).

The term "nonagronomic" refers to other horticultural crops (e.g., greenhouse, nursery or ornamental plants not grown in a field), residential and commercial structures in urban and industrial settings, turf (commercial, golf, residential, recreational, etc.), wood products, stored product, agroforestry and vegetation management, public health (human) and animal health (domestic animals, pets, livestock, poultry, undomestical animals such as wildlife) applications. For reasons of invertebrate pest control spectrum and economic importance, protection of agronomic crops from damage or injury caused by invertebrate pests by controlling invertebrate pests are embodiments of the invention.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Compounds of this invention exhibit activity against a wide spectrum of foliar-feeding, fruit-feeding, stem or root feeding, seed-feeding, aquatic and soil-inhabiting invertebrate pests which are pests of growing and stored agronomic crops, forestry, greenhouse crops, ornamentals, nursery crops, stored food and fiber products, livestock, household, public health and animal health. Those skilled in the art will appreciate that not all compounds are equally effective against all growth stages of all pests.

Agronomic or nonagronomic pests include eggs, larvae and adults of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Ainyelois transitella* Walker), corn root webworm (*Crambus caliginosellus* Clemens), sod webworms (Pyralidae: *Crambinae*) such as sod worm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus niaculicollis* Dietz), bluegrass billbug (*Sphenophorus parvulus* Gyllenhal), hunting billbug (*Sphenophorus venatus vestitus*), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgiferai* LeConte)); chafers and other beetles from the family Scaribaeidae (e.g., Japanese beetle (*Popillia japonica* Newman), oriental beetle (*Anomala orientalis* Waterhouse), northern masked chafer (*Cyclocephala borealis* Arrow), southern masked chafer (*Cyclocephala immaculata* Olivier), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae. Also included are eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, immatures and adults of the order Thysanoptera including onion thrips (*Thrips tabaci* Lindeman), flower thrips (*Frankliniella* spp.), and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say), bees (including carpenter bees), hornets, yellow jackets, wasps, and sawflies (*Neodiprion* spp.; *Cephus* spp.); insect pests of the Family Formicidae including the Florida carpenter ant (*Camponotus floridanus* Buckley), white-footed ant (*Technomyrmex albipes* fr. Smith), big headed ants (*Pheidole* sp.) and ghost ant (*Tapinoma melanocephalum* Fabricius); insect pests of the order Isoptera including termites in the Termitidae (ex. *Macrotermes* sp.), Kalotermitidae (ex. *Cryptotermes* sp.), and Rhinotermitidae (ex. *Reticulitermes* sp., *Coptotermes* sp.) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Mena-*

*canthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the invention also have significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Of note is use of compounds of this invention for controlling silverleaf whitefly (*Bemisia argentifolii*). Of note is use of compounds of this invention for controlling western flower thrip (*Frankliniella occidentalis*). Of note is use of compounds of this invention for controlling potato leafhopper (*Empoasca fabae*). Of note is use of compounds of this invention for controlling corn planthopper (*Peregrinus maidis*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling diamondback moth (*Plutella xylostella*).

Of note is use of compounds of this invention for controlling fall armyworm (*Spodoptera frugiperda*).

Compounds of this invention can also be mixed with one or more other biologically active compounds or agents including insecticides, fungicides, nematocides, bactericides, acaricides, herbicides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1 and an effective amount of at least one additional biologically active compound or agent and can further comprise at least one of a surfactant, a solid diluent or a liquid diluent. The other biologically active compounds or agents can be formulated in compositions comprising at least one of a surfactant, solid or liquid diluent. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metaminostrobin, metconazole, methasulfocarb, metiramzink, metominostrobin/fenominostrobin, mepanipyrim, metiram, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai*, *Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual*, 13*th Edition*, C. D. S. Tomlin, Ed., British Crop Protection Council, Farnham, Surrey, U.K., 2003 and *The BioPesticide Manual*, 2$^{nd}$ *Edition*, L. G. Copping, Ed., British Crop Protection Council, Farnham, Surrey, U.K., 2001.

In certain instances, combinations with other arthropodicides having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of this invention can also provide a broader spectrum of plant protection and be advantageous for resistance management.

In certain instances, combinations of a compound of this invention with other invertebrate pest control compounds or agents can result in a greater-than-additive (i.e. synergistic) effect and/or a less-than-additive effect (i.e. antagonistic). It is always desirable to reduce the quantity of chemical agents released in the environment while ensuring effective pest control. When synergism of invertebrate pest control agents is found at application rates giving agronomically satisfactory levels of pest control, such combinations can be advantageous for lowering crop production cost and reducing environmental load.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) of the invertebrate pest control agents. The third column of Table A lists embodiment(s) of ranges of weight ratios for rates at which the invertebrate pest control agent can be applied relative to a compound of Formula 1, an N-oxide, or a salt thereof, (e.g., "50:1 to 1:50" of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or chemical classes | Typical Weight Ratio |
| --- | --- | --- |
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Anthranilamides | ryanodine receptor ligands | 100:1 to 1:120 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Emamectin Benzoate | macrocyclic lactones | 50:1 to 1:10 |
| Endosulfan | cyclodiene insecticides | 200:1 to 1:100 |
| Esfenvalerate | sodium channel modulators | 100:1 to 1:400 |

TABLE A-continued

| Invertebrate Pest Control Agent | Mode of Action or chemical classes | Typical Weight Ratio |
| --- | --- | --- |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:200 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| NPV (e.g., Gemstar) | biological agents | 50:1 to 1:10 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta toxin | biological agents | 50:1 to 1:10 |
| *Beauvaria bassiana* | biological agents | 50:1 to 1:10 |

One embodiment of insecticides and acaricides for mixing with compounds of this invention include sodium channel modulators such as cypermethrin, cyhalothrin, cyfluthrin, beta-cyfluthrin, esfenvalerate, fenvalerate, indoxacarb and tralomethrin; cholinesterase inhibitors such as methomyl, oxamyl and thiodicarb; neonicotinoids such as acetamiprid, clothianidin, imidacloprid, thiacloprid and thiamethoxam; neuronal sodium channel blockers such as indoxacarb; insecticidal macrocyclic lactones such as spinosad, abamectin, avermectin and emamectin; GABA (γ-aminobutyric acid)-regulated chloride channel blockers such as endosulfan, ethiprole and fipronil; chitin synthesis inhibitors such as flufenoxuron and triflumuron; juvenile hormone mimics such as diofenolan and pyriproxyfen; octopamine receptor ligands such as amitraz; ecdysone agonists such as methoxyfenozide and tebufenozide; ryanodine receptor ligands such as ryanodine, anthranilamides and flubendiamide; fenothiocarb; flonicamid; metaflumizone; pyridalyl; and pymetrozine. One embodiment of biological agents for mixing with compounds of this invention include *Bacillus thuringiensis* and *Bacillus thuringiensis* delta-endotoxin as well as naturally occurring and genetically modified viral insecticides including members of the family Baculoviridae as well as entomophagous fungi.

The weight ratios of a compound, including a compound of Formula 1, an N-oxide or a salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Table B are embodiments of specific compositions comprising a compound of Formula 1 (compound numbers refer to compounds in Index Table A) and an additional invertebrate pest control agent.

TABLE B

| Mixture No. | Comp. No. | and | Invertebrate Pest Control Agent |
|---|---|---|---|
| A-1 | 1 | and | Abamectin |
| A-2 | 1 | and | Acetamiprid |
| A-3 | 1 | and | Amitraz |
| A-4 | 1 | and | Anthranilamides |
| A-5 | 1 | and | Avermectin |
| A-6 | 1 | and | Azadirachtin |
| A-7 | 1 | and | Beta-cyfluthrin |
| A-8 | 1 | and | Bifenthrin |
| A-9 | 1 | and | Buprofezin |
| A-10 | 1 | and | Cartap |
| A-11 | 1 | and | Chlorfenapyr |
| A-12 | 1 | and | Chlorpyrifos |
| A-13 | 1 | and | Clothianidin |
| A-14 | 1 | and | Cyfluthrin |
| A-15 | 1 | and | Cyhalothrin |
| A-16 | 1 | and | Cypermethrin |
| A-17 | 1 | and | Cyromazine |
| A-18 | 1 | and | Deltamethrin |
| A-19 | 1 | and | Dieldrin |
| A-20 | 1 | and | Dinotefuran |
| A-21 | 1 | and | Diofenolan |
| A-22 | 1 | and | Emamectin |
| A-23 | 1 | and | Emamectin Benzoate |
| A-24 | 1 | and | Endosulfan |
| A-25 | 1 | and | Esfenvalerate |
| A-26 | 1 | and | Ethiprole |
| A-27 | 1 | and | Fenothiocarb |
| A-28 | 1 | and | Fenoxycarb |
| A-29 | 1 | and | Fenvalerate |
| A-30 | 1 | and | Fipronil |
| A-31 | 1 | and | Flonicamid |
| A-32 | 1 | and | Flubendiamide |
| A-33 | 1 | and | Flufenoxuron |
| A-34 | 1 | and | Hexaflumuron |
| A-35 | 1 | and | Hydramethylnon |
| A-36 | 1 | and | Imidacloprid |
| A-37 | 1 | and | Indoxacarb |
| A-38 | 1 | and | Lambda-cyhalothrin |
| A-39 | 1 | and | Lufenuron |
| A-40 | 1 | and | Metaflumizone |
| A-41 | 1 | and | Methomyl |
| A-42 | 1 | and | Methoprene |
| A-43 | 1 | and | Methoxyfenozide |
| A-44 | 1 | and | Nitenpyram |
| A-45 | 1 | and | Nithiazine |
| A-46 | 1 | and | Novaluron |
| A-47 | 1 | and | NPV (e.g., Gemstar) |
| A-48 | 1 | and | Oxamyl |
| A-49 | 1 | and | Pymetrozine |
| A-50 | 1 | and | Pyrethrin |
| A-51 | 1 | and | Pyridaben |
| A-52 | 1 | and | Pyridalyl |
| A-53 | 1 | and | Pyriproxyfen |
| A-54 | 1 | and | Ryanodine |
| A-55 | 1 | and | Spinosad |
| A-56 | 1 | and | Spirodiclofen |
| A-57 | 1 | and | Spiromesifen |
| A-58 | 1 | and | Tebufenozide |
| A-59 | 1 | and | Thiacloprid |
| A-60 | 1 | and | Thiamethoxam |
| A-61 | 1 | and | Thiodicarb |
| A-62 | 1 | and | Tralomethrin |
| A-63 | 1 | and | Triazamate |

TABLE B-continued

| Mixture No. | Comp. No. | and | Invertebrate Pest Control Agent |
|---|---|---|---|
| A-64 | 1 | and | Triflumuron |
| A-65 | 1 | and | *Bacillus thuringiensis* |
| A-66 | 1 | and | *Bacillus thuringiensis* delta toxin |
| A-67 | 1 | and | *Beauvaria bassiana* |
| B-1 | 11 | and | Abamectin |
| B-2 | 11 | and | Acetamiprid |
| B-3 | 11 | and | Amitraz |
| B-4 | 11 | and | Anthranilamides |
| B-5 | 11 | and | Avermectin |
| B-6 | 11 | and | Azadirachtin |
| B-7 | 11 | and | Beta-cyfluthrin |
| B-8 | 11 | and | Bifenthrin |
| B-9 | 11 | and | Buprofezin |
| B-10 | 11 | and | Cartap |
| B-11 | 11 | and | Chlorfenapyr |
| B-12 | 11 | and | Chlorpyrifos |
| B-13 | 11 | and | Clothianidin |
| B-14 | 11 | and | Cyfluthrin |
| B-15 | 11 | and | Cyhalothrin |
| B-16 | 11 | and | Cypermethrin |
| B-17 | 11 | and | Cyromazine |
| B-18 | 11 | and | Deltamethrin |
| B-19 | 11 | and | Dieldrin |
| B-20 | 11 | and | Dinotefuran |
| B-21 | 11 | and | Diofenolan |
| B-22 | 11 | and | Emamectin |
| B-23 | 11 | and | Emamectin Benzoate |
| B-24 | 11 | and | Endosulfan |
| B-25 | 11 | and | Esfenvalerate |
| B-26 | 11 | and | Ethiprole |
| B-27 | 11 | and | Fenothiocarb |
| B-28 | 11 | and | Fenoxycarb |
| B-29 | 11 | and | Fenvalerate |
| B-30 | 11 | and | Fipronil |
| B-31 | 11 | and | Flonicamid |
| B-32 | 11 | and | Flubendiamide |
| B-33 | 11 | and | Flufenoxuron |
| B-34 | 11 | and | Hexaflumuron |
| B-35 | 11 | and | Hydramethylnon |
| B-36 | 11 | and | Imidacloprid |
| B-37 | 11 | and | Indoxacarb |
| B-38 | 11 | and | Lambda-cyhalothrin |
| B-39 | 11 | and | Lufenuron |
| B-40 | 11 | and | Metaflumizone |
| B-41 | 11 | and | Methomyl |
| B-42 | 11 | and | Methoprene |
| B-43 | 11 | and | Methoxyfenozide |
| B-44 | 11 | and | Nitenpyram |
| B-45 | 11 | and | Nithiazine |
| B-46 | 11 | and | Novaluron |
| B-47 | 11 | and | NPV (e.g., Gemstar) |
| B-48 | 11 | and | Oxamyl |
| B-49 | 11 | and | Pymetrozine |
| B-50 | 11 | and | Pyrethrin |
| B-51 | 11 | and | Pyridaben |
| B-52 | 11 | and | Pyridalyl |
| B-53 | 11 | and | Pyriproxyfen |
| B-54 | 11 | and | Ryanodine |
| B-55 | 11 | and | Spinosad |
| B-56 | 11 | and | Spirodiclofen |
| B-57 | 11 | and | Spiromesifen |
| B-58 | 11 | and | Tebufenozide |
| B-59 | 11 | and | Thiacloprid |
| B-60 | 11 | and | Thiamethoxam |
| B-61 | 11 | and | Thiodicarb |
| B-62 | 11 | and | Tralomethrin |
| B-63 | 11 | and | Triazamate |
| B-64 | 11 | and | Triflumuron |
| B-65 | 11 | and | *Bacillus thuringiensis* |
| B-66 | 11 | and | *Bacillus thuringiensis* delta toxin |
| B-67 | 11 | and | *Beauvaria bassiana* |

The specific mixtures listed in Table B typically combine a compound of Formula 1 with the other invertebrate pest agent in the ratios specified in Table A.

Invertebrate pests are controlled in agronomic and nonagronomic applications by applying a composition comprising a compound of this invention, in a biologically effective amount, to the environment of the pests, including the agronomic and/or nonagronomic locus of infestation, to the area to be protected, or directly on the pests to be controlled. Agronomic applications include protecting a field crop from invertebrate pests typically by applying a composition or a mixture of the invention to the seed of the crop before the planting, to the foliage, stems, flowers and/or fruit of crop plants, or to the soil or other growth medium before or after the crop is planted. Nonagronomic applications refer to invertebrate pest control in the areas other than fields of crop plants. Nonagronomic applications include control of invertebrate pests in stored grains, beans and other foodstuffs, and in textiles such as clothing and carpets. Nonagronomic applications also include invertebrate pest control in ornamental plants, forests, in yards, along roadsides and railroad rights of way, and on turf such as lawns, golf courses and pastures. Nonagronomic applications also include invertebrate pest control in houses and other buildings which may be occupied by humans and/or companion, farm, ranch, zoo or other animals. Nonagronomic applications also include the control of pests such as termites that can damage wood or other structural materials used in buildings.

Nonagronomic applications also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mange, mites and fleas. Internal parasites include heartworms, hookworms and helminths. Compounds and compositions of the present invention are particular suitable for combating external parasitic or disease transmitting pests.

Compounds and compositions of the present invention are suitable for combating parasites that infest agricultural working animals, such as cattle, sheep, goats, horses, pigs, donkeys, camels, buffalos, rabbits, hens, turkeys, ducks, geese and bees; pet animals and domestic animals such as dogs, cats, pet birds and aquarium fish; as well as so-called experimental animals, such as hamsters, guinea pigs, rats and mice. By combating these parasites, fatalities and performance reduction (in term of meat, milk, wool, skins, eggs, honey, etc.) are to be reduced, so that applying a composition comprising a compound of the present invention is intended to allow more economic and simple husbandry of animals.

Nonagronomic applications in the veterinary sector takes place in the known manner, by enteral administration in the form of, for example, tablets, capsules, drinks, drenching preparations, granulates, pastes, boli, feed-through procedures, suppositories; by parenteral administration, such as by injection (including intramuscular, subcutaneous, intravenous, intraperitoneal), implants; by nasal administration; by dermal administration, for example, in the form of immersion or dipping, spraying, pouring, washing, coating with powder, and through bodied devices such as neck collars, ear marks, tail marks, limb measuring tapes or halters which comprise compounds or compositions of the present invention.

Therefore, the present invention further comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the soil environment of the invertebrate pest with a biologically effective amount of a compound of the present invention. Of further note are compounds of this invention also effective by topical application to the locus of infestation. Other methods of contact include application of a compound or a composition of the invention by direct and residual sprays, aerial sprays, gels, seed coatings, nicroencapsulations, systemic uptake, baits, ear tags, boluses, foggers, fumigants, aerosols, dusts and many others. One embodiment of a method of contact is a dimensionally stable fertilizer granule, stick or tablet comprising a mixture or composition of the invention. The compounds of this invention can also be impregnated into materials for fabricating invertebrate control devices (e.g., insect netting). Seed coatings can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance, such as "Roundup Ready" seed.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1, an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest.

Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following Tests demonstrates the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A-E for compound descriptions. The following abbreviations are used in the Index Tables which follow: i is iso, Me is methyl, Et is ethyl and i-Pr is isopropyl. "(d)" means melts with apparent decomposition. The abbreviation "Ex." stands for "Example" and is followed by a number indicating in which example the compound is prepared.

INDEX TABLE A

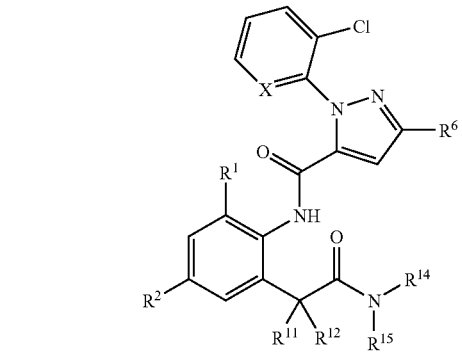

| Compound | $R^1$ | $R^2$ | $R^{11}$ | $R^{12}$ | $R^{14}$ | $R^{15}$ | $R^6$ | X | m.p. (° C.) |
|---|---|---|---|---|---|---|---|---|---|
| 1 (Ex. 1) | Me | H | H | H | i-Pr | H | $CF_3$ | N | 206-207 |
| 2 | Me | H | H | H | Me | H | $CF_3$ | N | 223-227 |

INDEX TABLE B

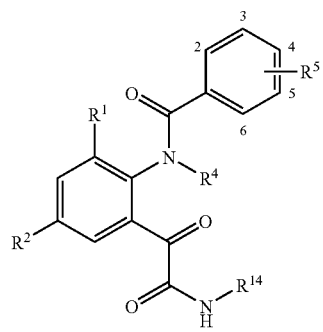

| Compound | $R^1$ | $R^2$ | $R^4$ | $R^{14}$ | $R^5$ | m.p. (° C.) |
|---|---|---|---|---|---|---|
| 3 | Me | Me | H | i-Pr | 4-$CF_3$ | 180-192 |

INDEX TABLE C

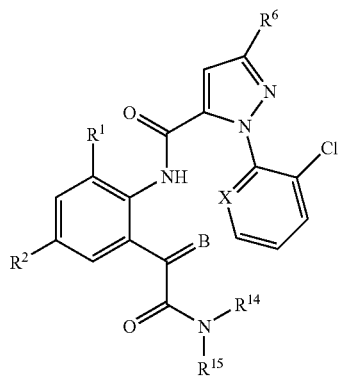

| Compound | R¹ | R² | B | R¹⁴ | R¹⁵ | R⁶ | X | m.p. (° C.) |
|---|---|---|---|---|---|---|---|---|
| 4 (Ex. 2) | Me | Me | O | Et | Et | CF₃ | N | ** |
| 5 | Me | Me | O | Me | Me | CF₃ | N | * |
| 6 (Ex. 3) | Me | Me | N—OH | Et | Et | CF₃ | N | ** |
| 7 | Me | Cl | O | Me | Me | CF₃ | N | * |
| 8 | Me | Cl | O | Et | Et | CF₃ | N | * |
| 9 | Me | Me | N—NHCO₂Me | Et | Et | CF₃ | N | * |
| 10 | Me | Me | N—OMe | Et | Et | CF₃ | N | * |
| 11 (Ex. 7) | Me | Cl | O | Me | H | Br | N | 246-247 |
| 12 (Ex. 6) | Me | Cl | (E)-N-Me | Me | H | Br | N | 230-234 (d) |
| 13 | Me | Cl | (Z)-N-Me | Me | H | Br | N | 239-241 (d) |

*See Index Table F for ¹H NMR data.
**See Examples for ¹H NMR data.

INDEX TABLE D

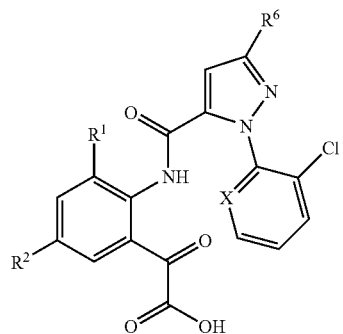

| Compound | R¹ | R² | R⁴ | R⁶ | X | m.p. (° C.) |
|---|---|---|---|---|---|---|
| 14 (Ex. 4) | Me | Cl | H | Br | N | 139-142 |

INDEX TABLE E

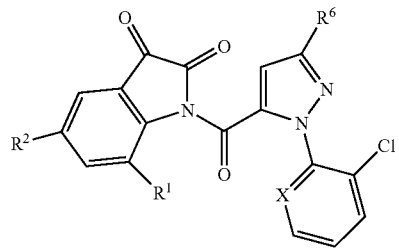

| Compound | R¹ | R² | R⁶ | X | m.p. (° C.) |
|---|---|---|---|---|---|
| 15 (Ex. 5) | Me | Cl | Br | N | 173-177 (d) |

INDEX TABLE F

| Cmpd No. | ¹H NMR Data (CDCl₃ solution unless indicated otherwise)[a] |
|---|---|
| 5 | 9.77 (br s, 1H), 8.44 (d, 1H), 7.85 (d, 1H), 7.48 (apparent s, 2H), 7.40 (dd, 1H), 7.26 (s, 1H), 2.96 (s, 3H), 2.84 (s, 3H), 2.32 (s, 3H), 2.14 (s, 3H). |
| 7 | 9.72 (s, 1H), 8.42 (d, 1H), 7.87 (d, 1H), 7.65 (d, 1H), 7.57 (s, 1H), 7.41 (dd, 1H), 7.39 (s, 1H), 2.94 (s, 3H), 2.85 (s, 3H), 2.12 (s, 3H). |
| 8 | 9.94 (s, 1H), 8.48 (d, 1H), 7.90 (d, 1H), 7.60 (d, 1H), 7.44 (s, 1H), 7.40 (dd, 1H), 7.39 (s, 1H), 3.49 (q, 2H), 3.18 (q, 2H), 2.19 (s, 3H), 1.22 (t, 3H), 1.13 (t, 3H). |
| 9 | 10.04 (br s, 1H), 8.79 (br s, 1H), 8.45 (d, 1H), 7.84 (d, 1H), 7.40 (dd, 1H), 7.08 (s, 1H), 6.90 (s, 1H), 3.87 (s, 3H), 3.48 (q, 2H), 2.91 (q, 2H), 2.26 (s, 3H), 2.21 (s, 3H), 1.20 (t, 3H), 0.74 (t, 3H). |
| 10 | major isomer: 9.99 (s, 1H), 8.47 (d, 1H), 7.86 (d, 1H), 7.42-7.38 (m, 2H), 7.06 (s, 1H), 7.02 (s, 1H), 3.94 (s, 3H), 3.49 (q, 2H), 3.2-3.07 (m, 2H), 2.26 (s, 3H), 2.18 (s, 3H), 1.26 (t, 3H), 0.99 (t, 3H). Also showed a minor oxime isomer. |

[a]¹H NMR data are in ppm downfield from tetramethylsilane. Couplings are designated by (s)—singlet, (d)—doublet, (t)—triplet, (q)—quartet, (m)—multiplet, (dd)—doublet of doublets, (dt)—doublet of triplets, (br s)—broad singlet.

BIOLOGICAL EXAMPLES OF THE INVENTION

Test A

For evaluating control of diamondback moth (*Plutella xylostella*) the test unit consisted of a small open container with a 12-14-day-old radish plant inside. This was pre-infested with 10-15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with ⅛ JJ custom body (Spraying Systems Co. Wheaton, Ill., USA) positioned 1.27 cm (0.5 inches) above the top of each test unit. Test compounds were sprayed at 50 ppm and replicated three times. After spraying of the formulated test compound, each test unit was allowed to dry for 1 hour and then a black, screened cap was placed on top. The test units were held for 6 days in a growth chamber at 25° C. and 70% relative humidity. Each test unit was visually assessed for insect mortality.

Of the compounds tested, the following resulted in at least 80% insect mortality: 1, 3, 4, 7, 8, 11, 12 and 14.

Test B

For evaluating control of fall armyworm (*Spodoptera frugiperda*) the test unit consisted of a small open container with a 4-5-day-old corn (maize) plant inside. This was pre-infested (using a core sampler) with 10-15 1-day-old larvae on a piece of insect diet.

Test compounds were formulated and sprayed at 50 ppm as described for Test A. The applications were replicated three times. After spraying, the test units were maintained in a growth chamber and then visually rated as described for Test A.

Of the compounds tested, the following resulted in at least 80% insect mortality: 1 and 11.

What is claimed is:

1. A compound of Formula 1, an N-oxide, or a salt thereof,

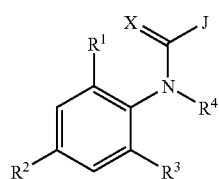

wherein
X is O or S;
J is a heterocyclic ring selected from the group consisting of

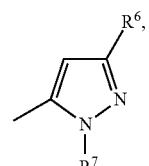
J-1

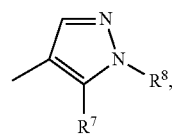
J-2

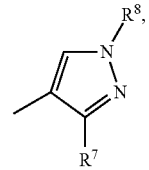
J-3

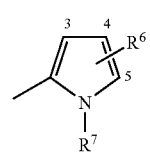
J-4

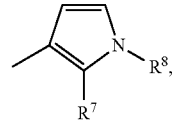
J-5

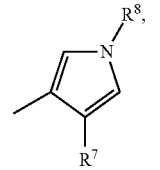
J-6

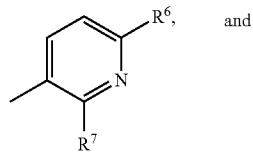
J-7  and

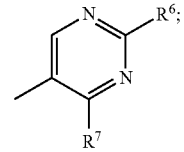
J-8

$R^1$ is $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, —CN, —CHO, —$NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_2$-$C_4$ alkylcarbonyl, $C_2$-$C_4$ alkoxycarbonyl, $C_2$-$C_4$ alkylaminocarbonyl, $C_3$-$C_5$ dialkylaminocarbonyl, $C_1$-$C_4$ alkylamino or $C_2$-$C_6$ dialkylamino;

$R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, —CN, —CHO, —NO$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_2$-$C_4$ alkylcarbonyl, $C_2$-$C_4$ alkoxycarbonyl, $C_2$-$C_4$ alkylaminocarbonyl, $C_3$-$C_5$ dialkylaminocarbonyl, $C_1$-$C_4$ alkylamino or $C_2$-$C_6$ dialkylamino;

$R^3$ is —C(=B)C(=O)L or —C($R^{11}R^{12}$)C(=O)L;

$R^4$ is H; or $C_1$-$C_6$ alkyl, $C_2$-$C_6$ alkenyl, $C_2$-$C_6$ alkynyl or $C_3$-$C_6$ cycloalkyl, each optionally substituted with one or more substituents selected from the group consisting of halogen, —CN, —NO$_2$, hydroxy, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^4$ is $C_2$-$C_6$ alkylcarbonyl, $C_2$-$C_6$ alkoxycarbonyl, $C_2$-$C_6$ alkylaminocarbonyl or $C_3$-$C_8$ dialkylaminocarbonyl; or $R^3$ and $R^4$ are taken together as —C(=B)C(=O)— or —C($R^{11}R^{12}$)C(=O)—, wherein the left-hand of these moieties is bonded as $R^3$ and the right-hand as $R^4$;

each $R^5$ is independently $C_1$-$C_6$ alkyl, $C_3$-$C_6$ cycloalkyl, $C_1$-$C_6$ haloalkyl, halogen, —CN, $C_1$-$C_4$ alkoxy, $C_1$-$C_4$ alkylthio, $C_1$-$C_4$ haloalkoxy, $C_1$-$C_4$ haloalkylthio, $C_1$-$C_4$ haloalkylsulfinyl or $C_1$-$C_4$ haloalkylsulfonyl; or phenyl or pyridyl, each optionally substituted with one to three $R^9$;

$R^6$ is H, $C_1$-$C_6$ alkyl, $C_3$-$C_6$ cycloalkyl, $C_1$-$C_6$ haloalkyl, halogen, —CN, $C_1$-$C_4$ alkoxy, $C_2$-$C_4$ alkoxycarbonyl, $C_1$-$C_4$ alkylthio, $C_1$-$C_4$ haloalkoxy, $C_1$-$C_4$ haloalkylthio, $C_1$-$C_4$ haloalkylsulfinyl or $C_1$-$C_4$ haloalkylsulfonyl;

$R^7$ is $C_1$-$C_6$ alkyl optionally substituted with one or more substituents selected from the group consisting of halogen, —CN, —NO$_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^7$ is phenyl or pyridyl, each optionally substituted with one to three substituents selected from $R^9$;

$R^8$ is H, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl;

each $R^9$ is independently $C_1$-$C_6$ alkyl, $C_3$-$C_6$ cycloalkyl, $C_1$-$C_6$ haloalkyl, halogen, —CN, $C_1$-$C_4$ alkoxy, $C_1$-$C_4$ alkylthio, $C_1$-$C_4$ haloalkoxy, $C_1$-$C_4$ haloalkylthio, $C_1$-$C_4$ haloalkylsulfinyl or $C_1$-$C_4$ haloalkylsulfonyl;

$R^{11}$ and $R^{12}$ are independently H; halogen; —CN; OR$^{13}$; or $C_1$-$C_6$ alkyl, $C_2$-$C_6$ alkenyl, $C_2$-$C_6$ alkynyl or $C_3$-$C_6$ cycloalkyl, each optionally substituted with one or more halogen;

B is O, NR$^{13}$, NOR$^{13}$ or NNR$^{14}R^{15}$;

L is OH or NR$^{14}R^{15}$;

$R^{13}$ is H; or $C_1$-$C_6$ alkyl, $C_2$-$C_6$ alkenyl, $C_2$-$C_6$ alkynyl or $C_3$-$C_6$ cycloalkyl, each optionally substituted with one or more halogen;

$R^{14}$ and $R^{15}$ are independently H; G; or $C_1$-$C_6$ alkyl, $C_2$-$C_6$ alkenyl or $C_2$-$C_6$ alkynyl, each optionally substituted with one or more substituents selected from the group consisting of G, halogen, —CN, —NO$_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_4$ alkylcarbonyl, $C_2$-$C_4$ alkoxycarbonyl, $C_1$-$C_4$ alkylamino, $C_2$-$C_8$ dialkylamino and $C_3$-$C_6$ cycloalkylamino; or $R^{14}$ and $R^{15}$ are taken together with the nitrogen to which they are attached to form a ring containing 2 to 6 atoms of carbon and optionally one additional atom of nitrogen, sulfur or oxygen, said ring optionally substituted with 1 to 4 substituents selected from the group consisting of $C_1$-$C_2$ alkyl, halogen, —CN, —NO$_2$ and $C_1$-$C_2$ alkoxy; and each G is independently a 3- to 6-membered nonaromatic carbocyclic or heterocyclic ring, optionally including one or two ring members selected from the group consisting of C(=O), S(O) or S(O)$_2$ and optionally substituted with 1 to 4 substituents selected from the group consisting of $C_1$-$C_2$ alkyl, halogen, —CN, —NO$_2$ and $C_1$-$C_2$ alkoxy.

2. The compound of claim 1 wherein $R^1$ is $C_1$-$C_4$ alkyl, $C_1$-$C_4$ haloalkyl, halogen, —CN, $C_1$-$C_4$ alkoxy or $C_1$-$C_4$ haloalkoxy;

$R^2$ is H, $C_1$-$C_4$ alkyl, $C_1$-$C_4$ haloalkyl, halogen, —CN, —CHO, —NO$_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $_2$-$C_4$ alkoxycarbonyl;

$R^3$ is —C(=O)C(=O)OH, —C($R^{11}R^{12}$)C(=O)OH, —C(=O)C(=O)NR$^{14}R^{15}$ or —C($R^{11}R^{12}$)C(=O)NR$^{14}R^{15}$; and $R^4$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl; or $R^3$ and $R^4$ are taken together as —C(=O)C(=O)—, —C(=NR$^{13}$)C(=O)— or —C($R^{11}R^{12}$)C(=O)—.

3. The compound of claim 2 wherein $R^1$ is CH$_3$, CF$_3$, OCF$_3$, OCHF$_2$, —CN or halogen;

$R^2$ is H, CH$_3$, CF$_3$, OCF$_3$, OCHF$_2$, S(O)$_p$CF$_3$, S(O)$_p$CHF$_2$, —CN or halogen;

$R^4$ is H; and p is 0, 1 or 2.

4. The compound of claim 3 wherein each $R^5$ is independently $C_1$-$C_4$ alkyl, $C_1$-$C_4$ haloalkyl, halogen, —CN, $C_1$-$C_4$ alkoxy or $C_1$-$C_4$ haloalkoxy;

each $R^6$ is independently $C_1$-$C_4$ haloalkyl, halogen, —CN or $C_1$-$C_4$ haloalkoxy;

$R^7$ is phenyl optionally substituted with one to three substituents independently selected from $R^9$; or $R^7$ is

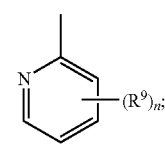

each $R^9$ is independently $C_1$-$C_4$ alkyl, $C_1$-$C_4$ haloalkyl, halogen or —CN;

$R^8$ is CH$_2$CF$_3$ or CHF$_2$; and n is 0, 1 or 2.

5. The compound of claim 3 wherein each $R^6$ is independently halogen, OCH$_2$CF$_3$, OCHF$_2$ or CF$_3$;

each $R^9$ is independently CH$_3$, CF$_3$, —CN or halogen.

6. The compound of claim 5 wherein

J is a heterocyclic ring selected from the group consisting of J-1, J-2 and J-3.

7. The compound of claim 6 wherein
$R^1$ is $CH_3$, F, Cl, Br or I;
$R^2$ is H, $CH_3$, $CF_3$, —CN, F, Cl, Br or I; and
each $R^6$ is independently Cl, Br, $OCH_2CF_3$ or $CF_3$.

8. The compound of claim 7 wherein $R^3$ is —C(=O)C(=O)OH.

9. The compound of claim 7 wherein $R^3$ is —C(=O)C(=O)$NR^{14}R^{15}$.

10. The compound of claim 1 that is selected from the group consisting of:
- 1-(3-chloro-2-pyridinyl)-N-[2-methyl-6-[2-(1-methylethyl)amino]-2-oxoethyl]phenyl]-3-(trifluoromethyl)-1H-pyrazole-5-carboxamide;
- 1-(3-chloro-2-pyridinyl)-N-[2-[(diethylamino)oxoacetyl]-4,6-dimethylphenyl]-3-(trifluoromethyl)-1H-pyrazole-5-carboxamide;
- 1-(3-chloro-2-pyridinyl)-N-[2-[(1Z)-2-(diethylamino)-1-(hydroxyimino)-2-oxoethyl]-4,6-dimethylphenyl]-3-(trifluoromethyl)-1H-pyrazole-5-carboxamide;
- 2-[[[3-bromo-1-(3-chloro-2-pyridinyl)-1H-pyrazol-5-yl]carbonyl]amino]-5-chloro-3-methyl-α-oxobenzeneacetic acid;
- 1-[[3-bromo-1-(3-chloro-2-pyridinyl)-1H-pyrazol-5-yl]carbonyl]-5-chloro-7-methyl-1H-indole-2,3-dione;
- 3-bromo-N-[4-chloro-2-methyl-6-(1E)-2-(methylamino)-1-(methylimino)-2-oxoethyl]phenyl]-1-(3-chloro-2-pyridinyl)-1H-pyrazole-5-carboxamide; and
- 3-bromo-N-[4-chloro-2-methyl-6-[(methylamino)oxoacetyl]phenyl]-1-(3-chloro-2-pyridinyl)-1H-pyrazole-5-carboxamide.

11. A composition for controlling an invertebrate pest comprising a biologically effective amount of a compound of claim 1 and at least one additional component selected from the group consisting of a surfactant, a solid diluent and a liquid diluent, said composition optionally further comprising a biologically effective amount of at least one additional biologically active compound or agent.

12. The composition of claim 11 in the form of a soil drench liquid formulation.

13. A bait composition for controlling an invertebrate pest, comprising:
(a) a biologically effective amount of the compound of claim 1 or the composition of claim 11;
(b) one or more food materials;
(c) optionally an attractant; and
(d) optionally a humectant.

14. A trap device for controlling an invertebrate pest, comprising:
(a) the bait composition of claim 13; and
(b) a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

15. A spray composition for controlling an invertebrate pest, comprising:
(a) a biologically effective amount of the compound of claim 1 or the composition of claim 11; and
(b) a propellant.

16. A method for controlling an invertebrate pest comprising contacting the invertebrate pest or its environment with a biologically effective amount of the compound of claim 1.

17. A method for controlling an invertebrate pest comprising contacting the invertebrate pest or its environment with the composition of claim 11.

18. The method of claim 17 wherein the environment is soil and the composition is applied to the soil as a soil drench formulation.

19. A method for controlling a cockroach, an ant or a termite, comprising contacting the cockroach, the ant, or the termite with the bait composition in the trap device of claim 14.

20. A method for controlling a mosquito, a black fly, a stable fly, a deer fly, a horse fly, a wasp, a yellow jacket, a hornet, a tick, a spider, an ant, or a gnat, comprising contacting the mosquito, the black fly, the stable fly, the deer fly, the horse fly, the wasp, the yellow jacket, the hornet, the tick, the spider, the ant, or the gnat with the spray composition of claim 15 dispensed from a spray container.

* * * * *